United States Patent [19]

Dreikorn et al.

[11] 4,407,820
[45] Oct. 4, 1983

[54] DIPHENYLAMINE COMPOUNDS

[75] Inventors: Barry A. Dreikorn, Lawrence; Kenneth E. Kramer, Indianapolis, both of Ind.

[73] Assignee: Eli Lilly and Company, Indianapolis, Ind.

[21] Appl. No.: 300,160

[22] Filed: Sep. 8, 1981

Related U.S. Application Data

[63] Continuation-in-part of Ser. No. 245,424, Mar. 19, 1981, abandoned.

[51] Int. Cl.³ .................... A01N 33/18; A01N 37/34; C07C 87/62; C07C 121/78
[52] U.S. Cl. ............................. 424/304; 260/465 E; 424/330; 564/433
[58] Field of Search .................... 260/465 E; 564/433; 424/304, 330

[56] References Cited

U.S. PATENT DOCUMENTS

| | | | |
|---|---|---|---|
| 4,117,167 | 9/1978 | Barlow et al. | 424/330 |
| 4,187,318 | 2/1980 | Dreikorn | 424/330 |
| 4,215,145 | 7/1980 | Grantham | 424/324 |
| 4,341,772 | 7/1982 | Grantham | 424/211 |

FOREIGN PATENT DOCUMENTS

| | | |
|---|---|---|
| 846205 | 3/1977 | Belgium . |
| 3259 | 12/1978 | European Pat. Off. . |
| 26743 | 4/1981 | European Pat. Off. . |
| 3044216 | 6/1982 | Fed. Rep. of Germany . |
| 68/4805 | of 1968 | South Africa . |
| 868165 | 4/1952 | United Kingdom . |
| 1525884 | 5/1976 | United Kingdom . |

OTHER PUBLICATIONS

*Agricultural Chem.*, Book 1, Insecticides, 1977 Revision, by W. T. Thompson, (Thompson Publications, Fresno, CA), pp. 76–77.

Derwent Abstract of EPO European Pat. Off. 26743, #27748 D/16.

Derwent Abstract of Germany 3,044,216, #50365 E/25.

*Primary Examiner*—Dolph H. Torrence
*Attorney, Agent, or Firm*—Kathleen R. S. Page; Arthur R. Whale

[57] ABSTRACT

The present invention is directed to the use of a class of N-alkyldiphenylamines as insecticides and arachnicides, and also as ectoparasiticides. The invention is also directed to a class of novel fluorinated N-alkyldiphenylamines.

51 Claims, No Drawings

DIPHENYLAMINE COMPOUNDS

CROSS-REFERENCE TO RELATED APPLICATION

This is a continuation-in-part of copending application Ser. No. 245,424, filed Mar. 19, 1981, abandoned.

BRIEF SUMMARY

The present invention is directed to methods employing certain diphenylamines for the control of insects, arachnides and ectoparasites.

The diphenylamines to be employed in accordance with the present invention are those compounds of the formula

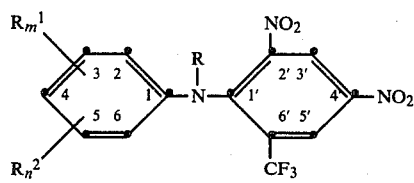

wherein

R = methyl, ethyl, or n-propyl; each $R^1$ is independently bromo, chloro, or fluoro;
$R^2$ is iodo, cyano, nitro, or trifluoromethyl;
m is an integer of from 0 to 5;
n is an integer of from 0 to 1;
and the sum of m and n is an integer
(1) when n is 0, from 1 to 5; and
(2) when n is 1, from 1 to 3
subject to the further limitations that (1) not more than two $R^1$ groups represent bromo; (2) where $R^2$=iodo, the iodo is located at the 4-position; (3) where $R^2$=cyano, the cyano is located at the 3-, 4-, or 5-position; and (4) where $R^2$=$NO_2$, the $NO_2$ is located at the 2-, 3-, 5-, or 6-position.

Certain of the present diphenylamines are claimed as novel compounds, and as components of novel formulations. These compounds are of the formula

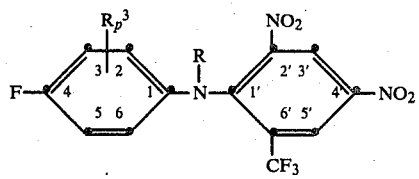

wherein R is, as above, methyl, ethyl, or n-propyl; and $R_p^3$ is one of the following:

(1) p=0;
(2) p=1 and $R^3$=2-F, 3-F, 2-Cl, or 2-Br;
(3) p=2 and $R^3$=2-F-6-Br or 2-F-6-Cl; or
(4) p=2, 3, or 4 and each $R^3$=F.

DETAILED DESCRIPTION

The compounds to be employed in accordance with the present invention are prepared in accordance with known procedures. Attention is directed to U.S. Pat. Nos. 4,117,167, and 4,187,318. In general, the compounds are prepared by one of the following reaction routes:

I. Condensation followed by alkylation:

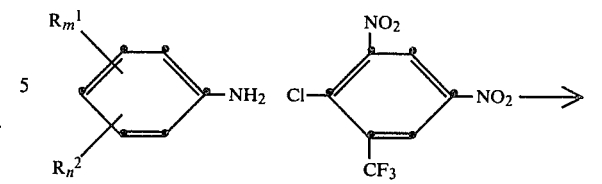

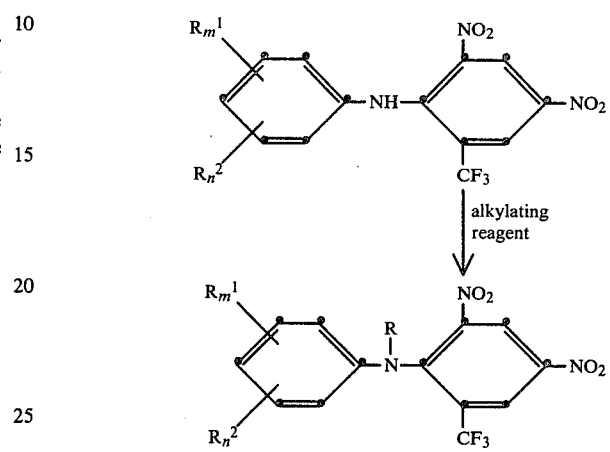

II. Halogenation of an N-alkyldiphenylamine (for compounds where one or more $R^1$ is bromo or chloro):

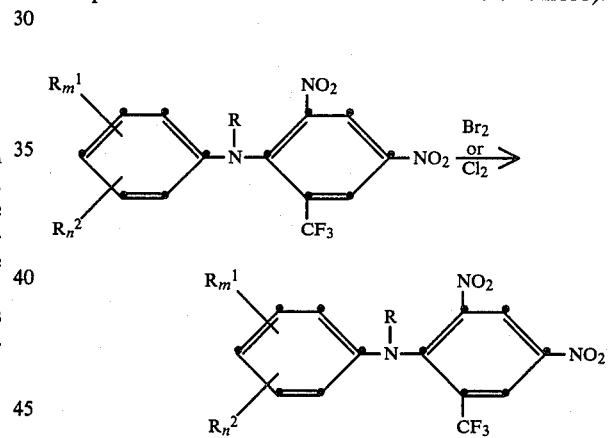

III. Nitration of an N-alkyldiphenylamine (where $R^2$ is $NO_2$):

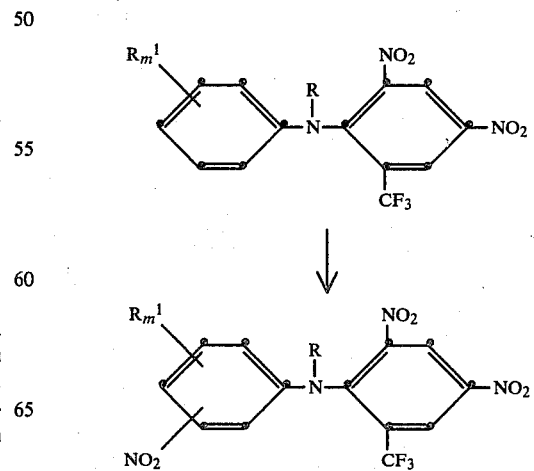

IV. Condensation of a 2-desnitrochlorobenzene and an N-alkylaniline, or an aniline with subsequent alkylation, followed by nitration of the 2'-position (for polyhalo-substituted compounds such as 2,4,6-trihalo-, tetrahalo-, and pentahalo-substituted compounds):

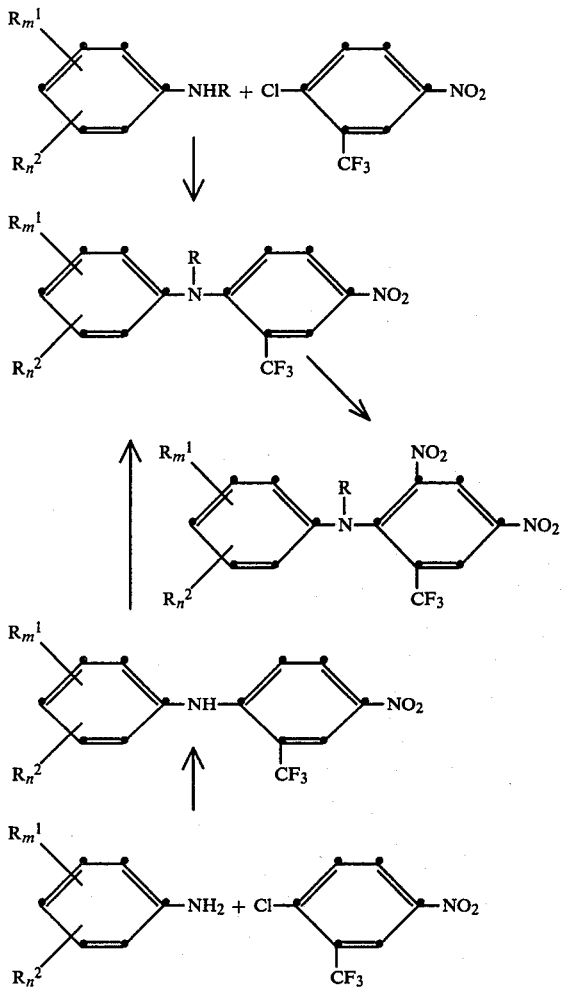

In addition to the foregoing procedures, it is believed that compounds of the present invention can be synthesized by an alternate method which in some instances may be preferred to the methods described above. In this synthetic route a fluorobenzene is prepared in situ from the corresponding chlorobenzene, and then condensed with an N-alkylaniline, yielding the desired N-alkyldiphenylamine directly:

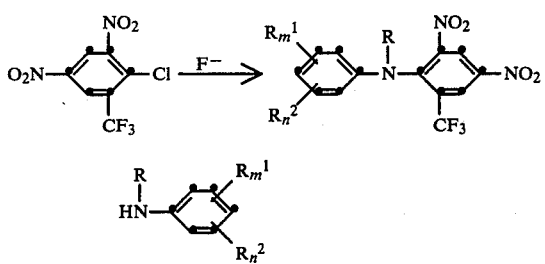

To date, the preferred source of fluoride is potassium fluoride, the preferred solvent is DMSO, and suitable reaction temperatures are 50°–100° C. The reactions can also be conducted with an aniline:

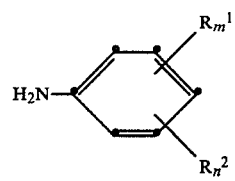

and the product alkylated to the desired N-alkyldiphenylamine.

The following examples illustrate the preparation of the compounds to be employed in accordance with the present invention.

EXAMPLE 1:
4-FLUORO-2',4'-DINITRO-6'-(TRIFLUOROMETHYL)DIPHENYLAMINE

4-Fluoroaniline (10.0 grams; 0.09 mole) was combined with 100 ml. of anhydrous ethanol. 1-Chloro-2,4-dinitro-6-(trifluoromethyl)benzene (12.2 grams; 0.045 mole) was added to the resulting solution, and the resulting reaction mixture was refluxed overnight (about 20 hours) under nitrogen. TLC indicated that the reaction had gone to completion. On cooling, a precipitate formed. It was separated by filtration and recrystallized from 75 ml. of ethanol. The identity of the product was confirmed by NMR, IR, and elemental analysis which showed Calculated for $C_{13}H_7F_4N_3O_4$: C, 45.23; H, 2.04; N, 12.17. Found: C, 45.29; H, 2.16; N, 12.21.

The total yield (two crops) was 11.9 grams (76.7%). The product melted at 135°–136° C.

EXAMPLE 2:
N-METHYL-4-FLUORO-2',4'-DINITRO-6'-(TRIFLUOROMETHYL)DIPHENYLAMINE

4-Fluoro-2',4'-dinitro-6'-(trifluoromethyl)diphenylamine 6.0 grams; 0.017 mole), acetone (50 ml.), sodium carbonate (16.4 grams), and dimethyl sulfate (16.4 ml.) were combined. The resulting reaction mixture was refluxed for 24 hours. TLC showed product plus starting material.

The reaction mixture was then worked up as follows. Water (100 ml.) was added and the reaction mixture heated for an additional hour. Additional water (200 ml.) was added and the mixture was allowed to cool and stand over a week-end (about 72 hours). The aqueous layer was then decanted off. The oily residue was dried by dissolving it in methylene chloride, treating the solution with anhydrous sodium sulfate, filtering, and stripping off the methylene chloride. The resulting material was purified by passing it through a silica gel column using toluene as eluent. The product fraction was collected and volatile material stripped off. The identity of the product was confirmed by NMR, IR, and elemental analysis, which showed Calculated for $C_{14}H_9F_4N_3O_4$: C, 46.81; H, 2.53; N, 11.70. Found: C, 47.00; H, 2.50; N, 11.71.

The product melted at 77°–78° C. and the yield was 4.53 grams (72.5%).

EXAMPLE 3:
N-METHYL-2,4-DIFLUORO-2',4'-DINITRO-6'-(TRIFLUOROMETHYL)DIPHENYLAMINE 2,4-Difluoro-2',4'-dinitro-6'-(trifluoromethyl)diphenylamine (2.6 grams; 0.0072 mole), acetone (18 ml.), sodium carbonate (6.8 grams), and dimethyl sulfate (6.8 ml.) were mixed. The reaction mixture was refluxed for four (4) hours. TLC indicated that the reaction had virtually gone to completion. Water (50 ml.) was added and the reaction mixture was heated for one hour. Additional water (100 ml.) was added and the reaction mixture was allowed to stir overnight (about 20 hours) at room temperature. The aqueous layer was then decanted off from the oil. Recrystallization of the oil from ethanol was unsuccessful, and the product was purified using a silica gel column, with toluene as the eluant. The identity of the product was confirmed by NMR and elemental analysis, which showed the following Calculated for $C_{14}H_8F_5N_3O_4$: C, 44.58; H, 2.14; N, 11.14. Found: C, 44.34; H, 2.36; N, 11.16.

The product melted at 108°–109° C. and the yield was 0.82 gram (30.2%).

EXAMPLE 4:
N-METHYL-2,4,6-TRIFLUORO-2',4'-DINITRO-6'-(TRIFLUOROMETHYL)DIPHENYLAMINE 2,4,6-Trifluoro-2',4'-dinitro-6'-(trifluoromethyl)diphenylamine (5.0 grams; 0.0131 mole), acetone (50 ml.), sodium carbonate (13.0 grams), and dimethyl sulfate (13 ml.) were mixed and refluxed for 24 hours. TLC indicated that there was still some unreacted starting material. The reaction mixture was then refluxed another 24 hours, with stirring. Water (200 ml.) was added, the reaction mixture heated for an additional hour, and another 200 ml. of water was added. The reaction mixture was permitted to cool and was left standing at room temperature for approximately 20 hours. The aqueous mixture was then decanted off from the oil. The oil was dissolved in methylene chloride, treated with anhydrous sodium sulfate and filtered, and the volatile components were stripped off.

The product was recrystallized from ethanol. Its identity was confirmed by NMR and elemental analysis, which showed the following Calculated for $C_{14}H_7F_6N_3O_4$: C, 42.55; H, 1.79; N, 10.63. Found: C, 42.30; H, 2.00; N, 10.45.

The product melted at 106°–108° C. and the yield was 1.50 grams (29.0%).

EXAMPLE 5:
N-METHYL-2-BROMO-4-FLUORO-2',4'-DINITRO-6'-(TRIFLUOROMETHYL)DIPHENYLAMINE

N-Methyl-4-fluoro-2',4'-dinitro-6'-(trifluoromethyl)diphenylamine (2.0 grams; 0.0056 mole), acetic acid (30 ml.), and bromine (1 ml.) were mixed. The reaction mixture was allowed to stir overnight (about 20 hours) at room temperature. TLC indicated that no reaction had taken place. Additional bromine (1 ml.) was added and the reaction mixture was refluxed for one hour. TLC again indicated that no reaction had taken place. Additional bromine (1 ml.) was added and the reaction mixture was refluxed for another three (3) hours, at which time TLC indicated that reaction had taken place. The reaction mixture was then permitted to stand over a weekend (about 72 hours) at room temperature. Water was added dropwise to fill the reaction flask (250 ml. size); the product precipitated and was separated by filtration and recrystallized from ethanol. The product melted at 160°–161.5° C. Its identity was confirmed by NMR and elemental analysis, which showed the following Calculated for $C_{14}H_8BrF_4N_3O_4$: C, 38.38; H, 1.84; N, 9.56. Found: C, 38.12; H, 2.05; N, 9.60.

The yield was 0.88 gram (36.1%).

EXAMPLE 6:
N-METHYL-2-NITRO-4-FLUORO-2',4'-DINITRO-6'-(TRIFLUOROMETHYL)DIPHENYLAMINE

N-methyl-4-fluoro-2',4'-dinitro-6'-(trifluoromethyl)diphenylamine (3.0 grams; 0.0084 mole) was dissolved in 50 ml. of trifluoroacetic acid. To this solution there was added by means of a dropping funnel, 0.60 gram (0.0075 mole) of ammonium nitrate dissolved in 15 ml. of trifluoroacetic acid. The reaction mixture was allowed to stir overnight (about 20 hours) at room temperature. Water was then added until the reaction flask (a 250 ml. size) was full. The product precipitated and was separated by filtration and recrystallized from ethanol. The product melted at 130.5°–132° C. Its identity was confirmed by NMR and elemental analysis, which showed the following Calculated for $C_{14}H_8F_4N_4O_6$: C, 41.60; H, 1.99; N, 13.86. Found: C, 41.59; H, 1.77; N, 13.71.

The yield was 0.85 gram (25.0%).

EXAMPLE 7:
N-ETHYL-2,4-DINITRO-6-(TRIFLUOROMETHYL)DIPHENYLAMINE 2,4-Dinitro-6-(trifluoromethyl)diphenylamine (14.4 grams; 0.044 mole), acetone (435 ml.), sodium carbonate (57.8 grams), and ethyl iodide (32 ml.) were combined and refluxed for a total of 4 days. The reaction was followed by TLC. After the first day, an additional 10 ml. of ethyl iodide was added. After the second day, an additional 10 ml. of ethyl iodide and 16 grams of sodium carbonate were added. After the third day, an additional 10 ml. of ethyl iodide and 15 grams of potassium carbonate were added.

At the end of the reflux period, the reaction mixture was allowed to cool, the precipitate was removed and discarded, and the filtrate was evaporated. The residue was separated into fractions on an HPLC. The identity of the product fraction was confirmed by NMR.

EXAMPLE 8:
N-ETHYL-2,4,6-TRICHLORO-2',4'-DINITRO-6'-(TRIFLUOROMETHYL)DIPHENYLAMINE

N-Ethyl-2,4-dinitro-6-(trifluoromethyl)diphenylamine (1.2 grams; 0.0034 mole) was dissolved in 100 ml. of acetic acid. Chlorine was bubbled in for two hours as the reaction mixture was refluxed. The reaction mixture was allowed to cool and the acetic acid removed by evaporation. The residue was taken up in methylene chloride and washed with a saturated aqueous solution of sodium bicarbonate. The methylene chloride layer was then dried over anhydrous sodium carbonate, filtered, and stripped of volatiles. The residue was a sticky solid. Its identity was confirmed by NMR which showed the following peaks: 8.66 ppm (doublet, indicating 3'-proton); 8.44 ppm (doublet, indicating 5'-proton); 7.32 ppm (singlet, indicating 3,5-protons); 3.94 ppm (quartet, indicating α-protons); and 1.20 ppm (triplet, indicating the β-protons).

EXAMPLE 9:
N-METHYL-2,3,4,5,6-PENTACHLORO-4'-NITRO-6'-(TRIFLUOROMETHYL)DIPHENYLAMINE

Sodium hydride (5.0 grams of a 57% oil dispersion) and 50 ml. of DMF (dried over molecular sieves) were combined and the resulting suspension was cooled to, and henceforth maintained at, between −10° and 0° C.

Nitrogen was passed over the reaction mixture throughout the reaction. A solution of N-methyl-2,3,4,5,6-pentachloroaniline (10.0 grams; 0.036 mole) in 50 ml. of DMF was added over a 10-minute period. The reaction mixture was allowed to stir for one hour. Then a solution of 2-chloro-5-nitrobenzotrifluoride (8.1 grams; 0.036 mole) in 50 ml. of DMF was added over a 15-minute period, and the reaction mixture was allowed to stir at room temperature for six hours.

The reaction mixture was then poured over ice and the volume adjusted to 1.8 l. with water. An oil formed; it was extracted with ether, dried, and the ether stripped off. The residual oil was recrystallized from hexane, m.p., 152°–154° C. Its identity was confirmed by NMR and elemental analysis, which showed the following Calculated for $C_{14}H_6Cl_5F_3N_2O_2$: C, 35.89; H, 1.29; N, 5.98. Found: C, 36.16; H, 1.35; N, 6.02.

EXAMPLE 10:
N-METHYL-2,3,4,5,6-PENTACHLORO-2',4'-DINITRO-6'-(TRIFLUOROMETHYL)DIPHENYLAMINE

N-Methyl-2,3,4,5,6-pentachloro-4'-nitro-6'-(trifluoromethyl)diphenylamine (1.85 grams; 0.0039 mole) was suspended in 40 ml. of trifluoroacetic acid. To this suspension there was added, by means of a dropping funnel, 0.37 gram (0.0044 mole) of ammonia nitrate in 12 ml. of trifluoroacetic acid. The reaction mixture was allowed to heat at 45°–50° C. for 2 hours, then 100 ml. of water was added, and the reaction mixture was allowed to stir overnight (about 20 hours) at room temperature. THe water was decanted off, leaving an oily residue which was recrystallized from ethanol, m.p., 159°–161° C. Its identity was confirmed by NMR and elemental analysis, which showed Calculated for $C_{14}H_5Cl_5F_3N_3O_4$: C, 32.75; H, 0.98; N, 8.18. Found: C, 33.07; H, 1.21; N, 8.25.
The yield was 0.74 gram (37.0%).

EXAMPLE 11:
N-METHYL-2,4-DIBROMO-2',4'-DINITRO-6'-(TRIFLUOROMETHYL)DIPHENYLAMINE 2,4-Dinitro-6-(trifluoromethyl)diphenylamine (11 grams; 0.034 mole), sodium carbonate (14 grams), dimethyl sulfate (6 ml.), and dioxane (to a total volume of 45 ml.), were stirred and refluxed for 24 hours. TLC indicated that the reaction was about 60% complete. Additional dimethyl sulfate (12 mls.) and sodium carbonate (10 grams) were added and the reaction continued for another two hours. The reaction mixture was then poured into water and stirred for four (4) hours. The supernatant was decanted and the residue was taken up in methylene chloride, separated from the water and filtered. To the resulting solution, containing 2,4-dinitro-6-(trifluoromethyl)-N-methyldiphenylamine, excess bromine was added and the reaction mixture was allowed to stand one hour, washed with water and sodium bicarbonate solution, filtered, and evaporated to dryness. The resulting residue was recrystallized from ethanol, m.p., 110° C. The yield was 11 grams (64.8%). The identity of the product was confirmed by NMR and elemental analysis, which showed Calculated for $C_{14}H_8Br_2F_3N_3O_4$: C, 33.70; H, 1.62; N, 8.42. Found: C, 33.95; H, 1.86; N, 8.32.

EXAMPLE 12:
N-ETHYL-3-(TRIFLUOROMETHYL)-2',4'-DINITRO-6'-(TRIFLUOROMETHYL)DIPHENYLAMINE

2-Chloro-3,5-dinitrobenzotrifluoride, (1.43 grams; 0.0053 mole), anhydrous potassium fluoride (3.0 grams; 0.0053 mole), DMSO dried over a molecular sieve (15 ml.), and N-ethyl-3-(trifluoromethyl)aniline (2.0 grams; 0.0106 mole) were mixed and allowed to heat from room temperature to 85° C. over a period of one hour. The reaction was followed by TLC.

After an hour and one half, the reaction mixture was allowed to cool and water was added to fill the reaction vessel (a 100 ml. flask). The reaction mixture was allowed to stand overnight (about 18 hours). The reaction mixture was extracted with three 100-ml. portions of ether, and the ether extract was treated with two 100-ml. portions of dilute ammonium hydroxide and three 100-ml. portions of dilute hydrochloric acid, then dried with sodium sulfate and filtered. The ether was removed by evaporation. The resulting product residue was an oil; it was purified over a silica gel column using toluene as the eluent. The product-containing fraction was collected and eluent removed. NMR showed solvent impurities from the eluent but otherwise confirmed the identity of the product. Elemental analysis showed Calculated for $C_{16}H_{11}F_9N_3O_4$: C, 45.40; H, 2.62; N, 9.93. Found (First Analysis): C, 47.23; H, 2.71; N, 9.29. Found (Second Analysis): C, 47.35; H, 2.85; N, 9.47.
The yield was 0.5 gram.

Other compounds to be employed in accordance with the present invention are prepared in analogous reactions and include those in the following table.

| EXAMPLE NUMBER | R | $R_m^1$ and $R_n^2$ | MELTING POINT (°C.) OR ELEMENTAL ANALYSIS | PERCENT YIELD |
| --- | --- | --- | --- | --- |
| 13 | $CH_3$ | 3-F | Calc. for $C_{14}H_9F_4N_3O_4$: Found: C,46.81;H,2.53;N,11.70. C,47.09;H,2.80;N,11.90. | 57.6 |
| 14 | $CH_3$ | 2-F | 83–84° | 67.6 |
| 15 | $CH_3$ | 2,5-di F | 109–110° | 26.5 |
| 16 | $CH_3$ | 3,4-di F | 91–93° | 74.6 |
| 17 | $CH_3$ | 2,6-di F | 95° | 28.4 |
| 18 | $CH_3$ | 2,3,5,6-tetra F | 94–95° | 50.7 |
| 19 | $CH_3$ | penta F | 114.5–115° | 22.5 |
| 20 | $CH_3$ | 4-Cl | 156–157° | 65.8 |
| 21 | $CH_3$ | 3-Cl | Calc. for $C_{14}H_9ClF_3N_3O_4$: Found: C,44.76;H,2.41;N,11.18. | 70.3 |

-continued

| EXAMPLE NUMBER | R | $R_m^1$ and $R_n^2$ | MELTING POINT (°C.) OR ELEMENTAL ANALYSIS | PERCENT YIELD |
|---|---|---|---|---|
| 22 | CH$_3$ | 2-Cl | C,44.71;H,2.21;N,11.18.<br>140–141° | 36.1 |
| 23 | CH$_3$ | 2,4,6-tri Cl | 120–121.5° | 34.6 |
| 24 | n-C$_3$H$_7$ | 2,4,6-tri Cl | Calc. for C$_{16}$H$_{11}$Cl$_3$F$_3$N$_3$O$_4$:<br>Found:<br>C,40.66;H,2.35;Cl,22.5;N,8.89.<br>C,40.66;H,2.22;Cl,22.45;N,8.71. | — (not recorded) |
| 25 | CH$_3$ | 4-Br | 167–168° | 95.2 |
| 26 | C$_2$H$_5$ | 4-Br | Calc. for C$_{15}$H$_{11}$BrF$_3$N$_3$O$_4$:<br>Found:<br>C,41.50;H,2.55;N,9.68.<br>C,41.27;H,2.63;N,9.45. | 8.6 |
| 27 | CH$_3$ | 3-Br | 87–89° | 39.0 |
| 28 | C$_2$H$_5$ | 2,4-di Br | 131–132° C. | 67.9 |
| 29 | CH$_3$ | 4-I | 163–164° | 65.2 |
| 30 | CH$_3$ | 4-CF$_3$ | 134–137° | 91.8 |
| 31 | CH$_3$ | 3-CF$_3$ | 108–109° | 48.9 |
| 32 | CH$_3$ | 2-Cl—5-CF$_3$ | Calc. for C$_{15}$H$_8$ClF$_6$N$_3$O$_4$:<br>Found:<br>C,40.61;H,1.82;N,9.47.<br>C,40.84;H,1.72;N,9.45. | 12.4 |
| 33 | CH$_3$ | 4-CN | 146–149° | 86.6 |
| 34 | C$_2$H$_5$ | 4-CN | 53–55° | 8.3 |
| 35 | C$_2$H$_5$ | 2,6-di Cl—4-CN | 118–120° | 21.0 |
| 36 | C$_2$H$_5$ | 2,4-di F | 75–76° | 3.6 |
| 37 | CH$_3$ | 3,5-di Cl | 107.5–108° | 73.2 |
| 38 | CH$_3$ | 2,4,6-tri Cl—3-F | 137–139° | 13.6 |
| 39 | CH$_3$ | 2,4-di Br—6-Cl | 139–141° | 78.7 |
| 40 | CH$_3$ | 3-CN | 109.5–110° | 56.8 |
| 41 | CH$_3$ | 2,6-di Br—4-F | 161.5–163° | 50.4 |
| 42 | CH$_3$ | 2-NO$_2$—4-Cl | 177.5–178.5° | 49.2 |
| 43 | CH$_3$ | 2-CF$_3$ | 148–149° | 3.7 |
| 44 | CH$_3$ | 2,6-di Cl—4-CF$_3$ | 98.5–99° | 68.5 |
| 45 | CH$_3$ | 2,4-di F—6-NO$_2$ | 102–103° | 46.1 |
| 46 | CH$_3$ | 2-Br—4-Cl | 131–133° | 23.8 |
| 47 | CH$_3$ | 2,6-di Br—4-Cl | 164.5–165.5° | 69.1 |
| 48 | CH$_3$ | 2,6-di Cl—4-F | 132–134° | 38.6 |
| 49 | CH$_3$ | 3-NO$_2$ | 112–113° | 65.2 |
| 50 | CH$_3$ | 3,4-di Cl | 107–109° | 49.4 |
| 51 | CH$_3$ | 2,4-di Cl | 97–99° | 14.4 |
| 52 | CH$_3$ | 3,4-di Br | 151–152° | 68.1 |
| 53 | CH$_3$ | 2-Br—4-F—6-Cl | 151–152° | 68.5 |
| 54 | CH$_3$ | 2,4-di F—6-Br | 144–145° | 48.8 |
| 55 | CH$_3$ | 2,4-di F—6-Cl | 123–124° | 57.0 |
| 56 | CH$_3$ | 2-Cl—4-F | 130–131° | 71.5 |

The novel compounds of the present invention include the following:

N-methyl-, ethyl-, or n-propyl-4-fluoro-2',4'-dinitro-6'-(trifluoromethyl)diphenylamine N-methyl-, ethyl-, or n-propyl-2,4-difluoro-2',4'-dinitro-6'-(trifluoromethyl)diphenylamine N-methyl-, ethyl-, or n-propyl-3,4-difluoro-2',4'-dinitro-6'-(trifluoromethyl)diphenylamine N-methyl-, ethyl-, or n-propyl-2-bromo-4-fluoro-2',4'-dinitro-6'-(trifluoromethyl)diphenylamine N-methyl-, ethyl-, or n-propyl-2-chloro-4-fluoro-2',4'-dinitro-6'-(trifluoromethyl)diphenylamine N-methyl-, ethyl-, or n-propyl-2,4,6-trifluoro-2',4'-dinitro-6'-(trifluoromethyl)diphenylamine N-methyl-, ethyl-, or n-propyl-2,3,4-trifluoro-2',4'-dinitro-6'-(trifluoromethyl)diphenylamine N-methyl-, ethyl-, or n-propyl-2,4,5-trifluoro-2',4'-dinitro-6'-(trifluoromethyl)diphenylamine N-methyl-, ethyl-, or n-propyl-3,4,5-trifluoro-2',4'-dinitro-6'-(trifluoromethyl)diphenylamine N-methyl-, ethyl-, or n-propyl-2,4-difluoro-6-bromo-2',4'-dinitro-6'-(trifluoromethyl)diphenylamine N-methyl-, ethyl-, or n-propyl-2,4-difluoro-6-chloro-2',4'-dinitro-6'-(trifluoromethyl)diphenylamine N-methyl-, ethyl-, or n-propyl-2,3,4,5-tetrafluoro-2',4'-dinitro-6'-(trifluoromethyl)diphenylamine N-methyl-, ethyl-, or n-propyl-2,3,4,6-tetrafluoro-2',4'-dinitro-6'-(trifluoromethyl)diphenylamine N-methyl-, ethyl-, or n-propyl-2,3,4,5,6-pentafluoro-2',4'-dinitro-6'-(trifluoromethyl)diphenylamine All of the present diphenylamines are useful for the control of phytophagous insects and arachnids. Therefore, the present invention is directed broadly to a method for inhibiting a phytophagous insect or arachnid which comprises applying to a locus of the insect or arachnid an effective insect- or arachnid-inhibiting amount of a diphenylamine in accordance with the present invention.

However, although the present compounds exhibit moderate insecticidal activity, they exhibit a higher order of activity against arachnids, especially the Acarina (mites). Therefore, in a preferred embodiment, the present invention is directed to a method for inhibiting a phytophagous mite which comprises applying to a plant a miticidally effective amount of a diphenylamine in accordance with the present invention.

Representative mite species with which the present invention can be practiced include those listed in the following table.

| Family | Scientific Name | Common Name |
| --- | --- | --- |
| ACARIDAE | | |
| | Aleurobius farinae | Flour mite |
| | Rhizoglyphus echinopus | Bulb mite |
| | Rhizoglyphus elongatus | Elongate mite |
| | Rhizoglyphus rhizophagus | Root mite |
| | Rhizoglyphus sagittatae | Balsam root mite |
| | Rhizoglyphus tarsalis | Beet mite |
| ERIOPHYIDAE | | |
| | Abacarus hystrix | |
| | Aceria brachytarsus | |
| | Aceria essigi | Redberry mite |
| | Aceria ficus | |
| | Aceria fraxinivorus | |
| | Aceria granati | |
| | Aceria parapopuli | Cottonwood mite |
| | Aceria sheldoni | Citrus bud mite |
| | Aceria tulipae | Wheat curl mite |
| | Aculus schlechtendali | Apple rust mite |
| | Eriophyes convolvens | |
| | Eriophyes insidiosus | |
| | Eriophyes malifoliae | Apple leaf mite |
| | Eriophyes padi | Plum twig gall mite |
| | Eriophyes pruni | Plum leaf gall mite |
| | Eriophyes pyri | Pear leaf blister mite |
| | Eriophyes ramosus | Juniper mite |
| | Eriophyes ribis | Currant gall mite |
| | Eriophyes vitis | Grape erineum mite |
| | Phyllocoptes gracilis | Blackberry mite |
| | Phyllocoptruta oleivora | Citrus rust mite |
| | Phytoptus avellanae | Filbert mite |
| | Phytoptus ribis | |
| | Trisetacus pini | Pine needle mite |
| | Vasates amygdalina | David peach mite |
| | Vasates cornutus | Peach silver mite |
| | Vasates eurynotus | Celery rust mite |
| | Vasates schlechtendali | Rusty leaf mite |
| EUPODIDAE | | |
| | Linopodes spp. | |
| PENTHALEIDAE | | |
| | Halotydeus destrustor | Redlegged earth mite Black sand mite |
| | Penthaleus major | Winter grain mite Blue oat mite |
| PYEMOTIDAE | | |
| | Siteroptes cerealium | |
| TARSONEMIDAE | | |
| | Steneotarsonemus pallidus | Cyclamen mite |
| TENUIPALPIDAE | | |
| | Brevipalpus californicus | California citrus mite |
| | Brevipalpus obovatus | |
| | Brevipalpus lewisi | Flat mite |
| | Tenuipalpes granati | |
| | Tenuipalpes pacificus | |
| TETRANYCHIDAE | | |
| | Bryobia arborea | Brown mite |
| | Bryobia rubrioculus | |
| | Eotetranychus coryli | |
| | Eotetranychus lewisi | Lewis spider mite |
| | Eotetranychus sexmaculatus | Six spotted spider mite |
| | Eotetranychus weldoni | Weldon's mite |
| | Eotetranychus willametti | |
| | Eutetranychus banksi | Texas citrus mite |
| | Mediolata mali | Apple mite |
| | Oligonychus ilicis | Southern red mite |
| | Oligonychus pratensis | Timothy mite, Banks grass mite |
| | Oligonychus ununguis | Spruce tree spider mite |
| | Panonychus citri | Citrus red mite |
| | Panonychus ulmi | European red mite |
| | Paratetranychus modestus | Corn mite |
| | Paratetranychus pratensis | Date mite |
| | Paratetranychus viridis | Green mite |
| | Petrobia decepta | Barley mite |
| | Schizotetranychus celarius | Bamboo mite |
| | Schizotetranychus pratensis | Alfalfa mite |
| | Tetranychus canadensis | Four spotted mite |
| | Tetrañychus cinnabarinus | |
| | Tetranychus mcdanieli | McDaniel mite |
| | Tetranychus pacificus | Pacific mite |
| | Tetranychus schoenei | Schoene mite |
| | Tetranychus telarius | Common red spider |
| | Tetranychus urticae | Two-spotted spider mite |
| | Tetranychus turkestani | Strawberry mite |
| | Tetranychus desertorum | Desert mite |

The present compounds are employed in manners conventional to known insecticides and arachnicides. A compound or compounds in accordance with the present invention is typically formulated with an adjuvant which is agriculturally acceptable to facilitate the present use of the compound or compounds. Thus, there can be employed as adjuvant water, an organic solvent, a surface active dispersing agent, an inert finely-divided solid, a propellant (as in an aerosol), a sticker which will insure adherence of a treating formulation to foliage, and the like. The use of a surface active dispersing agent is generally preferred; such formulations suitably contain from 0.1 to 95% of the present active agent.

The actual amount of compound to be applied to loci of insects and mites is not critical and can readily be determined by those skilled in the art in view of the examples below. In general, concentrations of from 10 ppm to 5,000 ppm of compound are expected to provide good control. With many of the compounds, concentrations of from 100 to 1,500 ppm will suffice. For field crops such as soybeans and cotton, a suitable application rate for the two most preferred compounds (defined below) is about 0.5 to 1.5 lbs./acre, typically applied in 50 gallons per acre of spray formulation containing 1200 to 3600 ppm of compound.

The locus to which a compound is applied can be any locus inhabited by a phytophagous insect or arachnid, for example, vegetable crops, fruit and nut trees, grape vines, and ornamental plants. Inasmuch as many mite species are specific to a particular host, the foregoing list of mite species also provide exemplification of the wide range of settings in which the present compounds can be used.

Because of the unique ability of mite eggs to resist toxicant action, repeated applications may be desirable to control newly emerged larvae, as is true of other known acaricides. However, as evidenced by the exemplary data below, at least some of the compounds have exhibited ovicidal effect.

The compounds to be employed in accordance with the present invention are advantageous in that they exhibit activity against mites resistant to the carbamate and organophosphate acaricides. A further advantage is that the compounds exhibit little or no phytotoxicity. Yet another advantage, as shown by Example 84, is that the compounds do not appear to induce resistance after multiple treatments.

As insecticides and arachnicides generally, and as acaricides in particular, certain of the present diphenylamines are preferred. Preferred compounds are those wherein R=methyl or ethyl, and especially those wherein R=methyl. Preferred substitution patterns on the

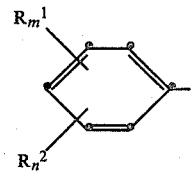

ring include 3-(trifluoromethyl), 4-fluoro, 4-bromo, 4-chloro, 2,4-difluoro, 2-chloro-4-fluoro, and 2-bromo-4-fluoro. The most preferred compounds appear to be N-methyl-3-(trifluoromethyl)-2',4'-dinitro-6'-(trifluoromethyl)diphenylamine and N-methyl-2,4-difluoro-2',4'-dinitro-6'-(trifluoromethyl)diphenylamine, and of these two, especially the latter.

The utility of the present compounds as insecticides and arachnicides is exemplified by the following examples.

EXAMPLE 57: MOSQUITO LARVICIDE TEST

Numerous compounds to be employed in the present invention were evaluated against late third or early fourth instar larvae of *Aedes aegypti* (Linne), Order Diptera, Family Culicidae. Test larvae five days old were allowed to feed on fresh food for at least three hours previous to being placed on test. Larvae were removed from the rearing pans by pouring on a 20 mesh screen, washing with deionized water, and pooling in a six-inch white enameled sauce pan. Larvae were then placed in one-oz paper cups containing 25 ml. of deionized water. Twenty larvae were placed in each cup.

Each compound to be evaluated was dissolved in a suitable solvent, typically a 50/50 mixture of reagent grade acetone and 95 to 100% ethyl alcohol containing Toximul R and Toximul S (each of Toximul R amd Toximul S is a sulfonate-nonionic blend of emulsifiers produced by Stepan Chemical Co.), and the solution was thereafter added to 225 ml. of deionized water. The 25 ml. of water containing 20 larvae were subsequently added, providing 250 ml. of test solution containing 20 ppm. of test compound. Results were determined 48 hours later by counting the dead and moribund larvae. The rating code employed was as follows:

| Number Larvae Dead and/or Moribund | | Rating | | % Dead |
|---|---|---|---|---|
| 0–2 | = | 0 | = | 0–10% |
| 3–4 | = | 1 | = | 15–20% |
| 5–6 | = | 2 | = | 25–30% |
| 7–8 | = | 3 | = | 35–40% |
| 9–10 | = | 4 | = | 45–50% |
| 11–12 | = | 5 | = | 55–60% |
| 13–14 | = | 6 | = | 65–70% |
| 15–16 | = | 7 | = | 75–80% |
| 17–18 | = | 8 | = | 85–90% |
| 19–20 | = | 9 | = | 95–100% |
| 20 Dead | = | 9+ | = | 100% |

TABLE I

MOSQUITO LARVICIDE TEST

| Compound of Example No. | Application Rate ppm. | Larvicidal Rating |
|---|---|---|
| 2 | 20 | 9 |
| " | 20 | 9 |
| " | 0.1 | 0 |
| 3 | 20 | 9 |
| " | 0.1 | 0 |
| 4 | 20 | 9 |
| " | 0.1 | 9 |
| " | 0.01 | 2 |
| " | 0.005 | 0 |
| 5 | 20 | 9 |
| 10 | 20 | 8 |
| 11 | 20 | 9 |
| 13 | 20 | 2 |
| " | " | 9 |
| 14 | 20 | 9 |
| " | 0.1 | 8 |
| 15 | 20 | 9 |
| " | 0.1 | 0 |
| 17 | 20 | 9 |
| " | 0.1 | 9 |
| " | 0.01 | 4 |
| " | 0.005 | 0 |
| 20 | 20 | 9 |
| 23 | 20 | 9 |
| " | 0.1 | 9 |
| " | 0.01 | 9 |
| " | 0.005 | 9 |
| 25 | 20 | 9 |
| 28 | 20 | 9 |
| " | 0.1 | 9 |
| " | 0.01 | 9 |
| " | 0.005 | 9 |
| 30 | 20 | 9 |
| 33 | 20 | 9 |
| " | 0.1 | 4 |
| 37 | 20 | 0 |
| 39 | 20 | 9 |
| 40 | 20 | 9 |
| " | 0.1 | 0 |
| 41 | 20 | 9 |
| 44 | 20 | 9 |
| 45 | 20 | 9 |
| 47 | 20 | 9 |
| 48 | 20 | 9 |
| 50 | 2 | 9 |
| " | 1 | 9 |
| " | 0.01 | 7 |
| 51 | 2 | 9 |
| " | 1 | 9 |
| " | 0.01 | 8 |
| 52 | 2 | 9 |
| " | 1 | 9 |
| " | 0.01 | 3 |
| 53 | 2 | 9 |
| " | 1 | 9 |
| " | 0.01 | 4 |

TABLE I-continued

MOSQUITO LARVICIDE TEST

| Compound of Example No. | Application Rate ppm. | Larvicidal Rating |
|---|---|---|
| 54 | 2 | 9 |
| " | 1 | 9 |
| " | 0.01 | 9 |
| 55 | 2 | 9 |
| " | 1 | 9 |
| " | 0.01 | 7 |
| 56 | 2 | 9 |
| " | 1 | 9 |
| " | 0.01 | 1 |

EXAMPLE 58: MITE-INSECT SCREEN

Numerous of the compounds to be employed in the present invention were evaluated against four insect and mite species, with test procedures as set forth below. Each compound was formulated in essentially the same procedures set forth above for the Mosquito Larvicide Test.

MEXICAN BEAN BEETLE & SOUTHERN ARMYWORM

Bountiful green beans were grown from seed to 4- to 6-day-old plants. They were then sprayed with a formulation containing the test compound at 1000 ppm or lesser concentration; the spraying was of both the tops and bottoms of the leaves, about 8–10 ml. per plant. The plants were then allowed to dry and the leaves removed.

Some of the leaves were placed in 100×20 mm plastic petri dishes containing second instar larvae of Mexican Bean Beetle (*Epilachna varivestis* Mulsant, order Coleoptera, family Coccinellidae), two leaves (approximately 6 sq. in. of leaf surface) and five larvae per petri dish. Two replicates were carried out per treatment. A small pad of cellulose was added to each dish to help prevent the leaves from wilting.

Other treated leaves were placed in 100×20 mm plastic petri dishes containing third instar larvae of Southern Armyworm (*Spodoptera eridania* Cramer, order Lepidoptera, Family Noctuidae).

A solvent control and an untreated control were also employed, as well as a reference standard for each species.

For both species, mortality counts were made four days after the larvae were placed on the treated leaves, using the following scale:

| Actual No. of dead larvae | Rating |
|---|---|
| 0 | 0 |
| 1–2 | 1 |
| 3–4 | 2 |
| 5 | 3 |

In some tests, the amount of feeding by the larvae was also rated, on the following scale:

| Feeding | Rating |
|---|---|
| none | 0 |
| 1–50% of leaves | 1 |
| 50–99% of leaves | 2 |
| 100% of leaves | 3 |

TWO-SPOTTED SPIDER MITE

Young Blue hubbard squash plants were thinned to one cotyledon per plant and infested by placing on each cotyledon a bean leaf infested with two-spotted spider mite (*Tetranychus urticae* (Koch), Order Acarina, family Tetranychidae). The plants were held for a day, then sprayed to wetting with a formulation containing 1000 ppm or lesser concentration of the test compound, with one infested plant (cotyledon) per treatment. Mortality was determined four days after treatment, using the following rating scale:

| Percent Dead | Rating |
|---|---|
| 0 | 0 |
| 1–50 | 1 |
| 51–99 | 2 |
| 100 | 3 |

HOUSEFLY

A cage of about 100 houseflies (*Musca domestica* (Linne), Order Diptera, Family Muscidae) was sprayed with 5 ml. of a formulation containing 1000 ppm or lesser concentration of the test compound. A knockdown count was made 2 hours later, after which the flies were supplied a 5% solution of sugar in water. A mortality count was made 24 hours after treatment. Both knockdown and mortality counts employed the same rating system employed in the two-spotted spider mite test. An untreated control, a solvent control, and a reference standard were employed.

Results of the foregoing tests were as set forth in the following table. For the Mexican Bean Beetle and Southern Armyworm species, each of the two replicates is reported separately.

TABLE II

MITE-INSECT SCREEN

| Compound of Example No. | Appln. Rate ppm. | Mexican Bean Beetle Mortality Rating | Mexican Bean Beetle Feeding Rating | Southern Armyworm Mortality Rating | Southern Armyworm Feeding Rating | Two-spotted Spider Mite Mortality Rating | Housefly Mortality Rating Contact | Housefly Mortality Rating Knockdown |
|---|---|---|---|---|---|---|---|---|
| 2 | 1000 | 3,3 | 0,0 | 0,0 | | 3 | | |
|   | 1000 | 3,2 | 1,1 | 0,0 | | 3 | | |
|   | 100 | 0,0 | | | | 0 | | |
|   | 1000 | 3,3 | 1,1 | | | 0 | | |
| 3 | 1000 | 3,3 | 0,0 | 3,3 | 1,0 | 3 | | |
|   | 10 | 1,0 | | 0,0 | | 0 | | |
|   | 100 | 3,3 | 1,1 | 1,0 | | 3 | 3 | 2 |

TABLE II-continued

MITE-INSECT SCREEN

| Compound of Example No. | Appln. Rate ppm | Mexican Bean Beetle Mortality Rating | Feeding Rating | Southern Armyworm Mortality Rating | Feeding Rating | Two-spotted Spider Mite Mortality Rating | Housefly Mortality Rating Contact | Knockdown |
|---|---|---|---|---|---|---|---|---|
|  | 1000 | 3,3 | 0,0 | 3,3 | 0,0 | 3 | 3 | 3 |
|  | 10 | 0,0 |  | 0,0 |  | 0 |  |  |
|  | 100 | 0,0 |  | 0,0 |  | 0 |  |  |
| 4 | 1000 | 3,3 | 0,0 | 3,3 | 0,0 | 3 |  |  |
|  | 1000 | 3,3 | 0,0 | 3,3 | 0,0 | 0 |  |  |
|  | 100 | 1,1 |  | 3,3 | 0,0 |  |  |  |
|  | 10 |  |  | 0,0 |  |  |  |  |
|  | 100 | 0,0 |  | 3,3 | 0,0 | 3 |  |  |
|  | 1000 | 3,3 | 0,0 | 3,3 | 0,0 | 3 |  |  |
| 5 | 100 | 1,0 |  | 0,0 |  |  |  |  |
|  | 1000 | 3,3 | 0,1 | 3,3 | 0,0 | 0 |  |  |
|  | 10 | 0,0 |  | 0,0 |  | 3 |  |  |
|  | 100 | 2,2 | 1,1 | 1,0 |  | 3 |  |  |
|  | 1000 | 3,3 | 0,0 | 3,3 | 0,0 | 2 |  |  |
| 6 | 10 | 1,0 |  | 0,0 |  | 0 |  |  |
|  | 100 | 0,0 |  | 0,0 |  | 0 |  |  |
|  | 1000 | 0,0 |  | 3,3 | 0,0 | 1 |  |  |
| 10 | 1000 | 3,3 | 0,0 | 3,3 | 1,1 | 0 |  |  |
|  | 1000 | 3,3 | 1,1 | 3,2 | 1,1 | 2 |  |  |
|  | 100 | 0,0 |  |  |  |  |  |  |
| 11 | 1000 | 3,3 | 1,1 | 3,3 | 0,1 | 3 |  |  |
|  | 1000 | 3,3 | 1,1 | 3,3 | 0,0 | 2 |  |  |
|  | 100 | 3,1 | 1 | 3,3 | 1,0 | 1,1 |  |  |
|  | 1000 | 3,3 | 1,0 | 3,3 | 0,0 | 3,3 | 3 | 0 |
|  | 10 | 0,0 |  | 0,0 |  |  | 2 | 2 |
|  | 100 | 2,3 |  | 3,3 |  |  | 2 | 2 |
|  | 100 | 3,3 | 0,1 |  |  |  |  |  |
|  | 10 | 0,0 |  |  |  |  |  |  |
| 13 | 1000 | 2,3 | 1,1 | 0,0 |  | 3 |  |  |
| 14 | 1000 | 3,3 | 0,0 | 2,1 | 1 | 0 |  |  |
|  | 1000 | 3,3 | 0,0 | 2,3 | 0 | 2 |  |  |
|  | 100 | 0,0 |  |  |  |  |  |  |
|  | 1000 | 3,3 | 1,1 |  |  |  |  |  |
|  | 100 | 1,0 |  | 0,0 |  |  |  |  |
| 15 | 1000 | 3,3 | 0,1 | 3,3 | 0,0 | 0 |  |  |
|  | 1000 | 3,3 | 0,0 | 3,3 | 0,0 | 3 |  |  |
|  | 10 | 0,0 |  | 0,0 |  | 0 |  |  |
|  | 100 | 1,0 |  | 1,1 | 1,1 | 0 | 2 | 1 |
|  | 1000 | 3,3 | 0,1 | 3,3 | 0,0 | 0 | 3 | 3 |
|  | 100 | 1,1 |  | 1,3 | 0 |  |  |  |
| 16 | 1000 | 3,3 | 0,0 | 2,3 | 0,0 | 3 |  |  |
|  | 1000 | 3,3 | 1,1 | 3,3 | 0,0 | 3 |  |  |
|  | 100 | 1,1 |  |  |  |  |  |  |
|  | 1000 | 3,3 | 0,1 |  |  |  |  |  |
|  | 100 | 0,0 |  | 2,0 |  |  |  |  |
| 17 | 1000 | 3,3 | 0,0 | 3,3 | 0,0 | 3 |  |  |
|  | 100 | 1,0 |  | 2,0 |  |  |  |  |
| 18 | 1000 | 3,3 | 0,0 | 3,3 | 0,0 | 2 |  |  |
|  | 1000 | 3,3 | 1,0 | 3,3 | 0,0 | 3 |  |  |
|  | 100 | 0,0 |  | 2,3 | 1,0 |  |  |  |
|  | 100 | 1,1 |  | 3,3 | 0,0 | 0 | 0 |  |
|  | 1000 | 3,3 | 0,0 | 3,3 | 0,0 | 2 | 3 |  |
| 19 | 1000 | 1,1 |  | 3,3 | 0,0 | 3 |  |  |
|  | 100 |  |  | 3,3 | 0,0 |  |  |  |
|  | 10 |  |  | 0,0 |  |  |  |  |
| 20 | 1000 | 2,3 |  | 1,1 |  | 2 |  |  |
|  |  | 0,0 |  | 0,0 |  | 0 |  |  |
| 21 | 1000 | 3,3 | 1,1 | 2,2 |  | 3 |  |  |
|  | 100 | 0,0 |  |  |  |  |  |  |
| 22 | 1000 | 3,3 | 1,1 | 1,1 | 1 | 1 |  |  |
|  | 100 | 1,1 |  |  |  |  |  |  |
| 23 | 1000 | 3,3 | 0,0 | 3,3 | 0,0 | 3,3 | 3 | 3 |
|  | 1000 | 2,2 | 1,1 | 3,2 | 0,0 | 1,2 |  |  |
|  | 1000 | 3,3 | 0,0 | 3,3 | 0,0 | 0 |  |  |
|  | 1000 | 3,3 | 1,1 | 3,3 | 0,0 | 3 |  |  |
|  | 100 | 2,1 |  | 3,3 | 0,1 | 1,1 | 2 | 0 |
|  | 10 | 0,0 |  | 0,0 |  | 0,0 |  |  |
|  | 100 | 0,1 |  | 3,3 | 0,0 |  |  |  |
|  | 10 |  |  | 0,0 |  |  |  |  |
| 25 | 1000 | 0,0 |  | 0,1 |  | 3 |  |  |
|  | 1000 | 1,1 |  | 1,1 | 1 | 3 |  |  |
| 27 | 1000 | 3,3 | 1,1 | 3,2 | 1,1 | 3 |  |  |
|  | 100 | 0,0 |  | 0,0 |  |  |  |  |
| 28 | 1000 | 3,3 | 1,0 | 3,3 | 0,1 | 3 |  |  |
|  | 100 | 3,3 | 1,0 | 3,3 |  |  | 3 | 2 |
|  | 1000 | 3,3 |  | 3,3 | 0,0 |  | 3 | 3 |

TABLE II-continued
MITE-INSECT SCREEN

| Compound of Example No. | Appln. Rate ppm. | Mexican Bean Beetle Mortality Rating | Mexican Bean Beetle Feeding Rating | Southern Armyworm Mortality Rating | Southern Armyworm Feeding Rating | Two-spotted Spider Mite Mortality Rating | Housefly Mortality Rating Contact | Housefly Mortality Rating Knockdown |
|---|---|---|---|---|---|---|---|---|
| | 10 | 0 | 0 | 0 | 0 | | 0 | 0 |
| | 100 | 1 | 1 | 3 | 3 | | 3 | 3 |
| 29 | 1000 | 1,1 | | 2,2 | | 3 | | |
| 30 | 1000 | 3,3 | 1,0 | 1,1 | | 3 | | |
| | 1000 | 3,3 | | 2,3 | 1,0 | 3 | | |
| | 100 | 2,2 | 1,1 | 0,0 | | 0 | | |
| | 1000 | 3 | 0 | 3 | 0 | 3 | | |
| | 100 | 1,0 | | | | | | |
| 31 | 1000 | 3,3 | 0,0 | 3,3 | 0,0 | 3 | | |
| | 100 | 1,0 | | 0,0 | | | | |
| 32 | 1000 | 1,0 | | 3,3 | 0,0 | 3 | | |
| | 100 | | | 0,1 | | | | |
| 33 | 1000 | 2,3 | 1,1 | 0,0 | | 0 | | |
| | 1000 | 1,1 | | 0,0 | | 3 | | |
| | 100 | 0,0 | | | | | | |
| | 1000 | 3 | 1 | | | | | |
| 35 | 1000 | 3,3 | 1,1 | 0,0 | | 0 | | |
| | 100 | 0,0 | | | | | | |
| 37 | 1000 | 1,1 | | 3,3 | 1,0 | 0 | | |
| | 1000 | 0,0 | | 3,3 | 0,0 | 0 | | |
| | 10 | 0,0 | | 0,0 | 0,0 | 0 | 2 | 2 |
| | 100 | 0,2 | 1 | 3,2 | 0,0 | 2 | 3 | 3 |
| | 1000 | 3,3 | 1 | 3,3 | | | | |
| | 100 | | | 3,2 | 0,0 | | | |
| | 1000 | | | 3,3 | 0,0 | | | |
| 38 | 1000 | 3,3 | 1,1 | 3,2 | 0,1 | 2 | | |
| | 100 | 0,0 | | 0,0 | | | | |
| 39 | 1000 | 3,3 | 1,0 | 3,3 | 1,0 | 0 | | |
| | 1000 | 0,3 | 1 | 3,3 | 0,0 | | | |
| | 1000 | 3,3 | 0,0 | 3,3 | 0,0 | 3 | | |
| | 100 | 0,0 | | 0,0 | | | | |
| | 100 | 0,0 | | 1,0 | | | | |
| 40 | 1000 | 3,3 | 1,0 | 0,1 | | 3 | | |
| | 1000 | 3,3 | 1,1 | 0,0 | | 2 | | |
| | 100 | 0,0 | | | | | | |
| 41 | 1000 | 3,2 | 1,1 | 3,3 | 0,1 | 2 | | |
| | 100 | 0,0 | | 0,0 | | | | |
| | 1000 | 0,0 | | 3,3 | 0,0 | 0 | | |
| 42 | 1000 | 0,0 | | 3,3 | 1,1 | 1 | | |
| | 100 | | | 1,2 | | | | |
| 43 | 1000 | 0,0 | 1 | 1,1 | | 1 | | |
| 45 | 1000 | 3,3 | 0,0 | 3,3 | 0,0 | 3 | | |
| | 100 | 1,0 | | 1,0 | | 0 | 3 | 0 |
| | 1000 | 3,3 | 1,1 | 3,3 | 0,0 | 0 | 3 | 2 |
| | 10 | | | | | 0 | 0 | 0 |
| | 100 | 0 | 0 | 0 | 0 | 0 | 3 | 1 |
| | 100 | 0,0 | | 0,0 | | 0 | | |
| | 1000 | 3,3 | 0,1 | 3,3 | 1,1 | 1 | | |
| | 10 | 1,0 | | 0,0 | | 0 | | |
| | 100 | 0,1 | | 0,0 | | 0 | | |
| | 10 | 1,1 | | 0,0 | | 0 | | |
| | 100 | 0,0 | | 1,0 | | 0 | | |
| | 1000 | 3,3 | 1,1 | 3,3 | 0,0 | 3 | | |
| 45 | 1000 | 2,2 | | 3,3 | 0,0 | 3 | | |
| | 10 | 0,0 | | 0,0 | | 0 | | |
| | 100 | 0,0 | | 2,2 | 1,1 | 3 | | |
| | 1000 | 1,1 | 1,1 | 3,3 | 0,0 | 3 | | |
| 47 | 1000 | 0,0 | | 3,3 | 0,0 | 3 | | |
| | 10 | 0,0 | | 0,0 | | 3 | | |
| | 100 | 0,0 | | 0,0 | | 1 | | |
| | 1000 | 0,0 | | 3,3 | 0,0 | 1 | | |
| | 100 | 0,0 | | 2,2 | | 0 | | |
| | 1000 | 1,0 | | 3,3 | | 1 | | |
| 48 | 1000 | 1,0 | | 3,3 | 0,0 | 0 | | |
| | 10 | 0,0 | | 0,0 | | 1 | | |
| | 100 | 2,1 | 1,1 | 2,2 | 0,1 | 1 | | |
| | 1000 | 3,3 | 0,0 | 3,3 | 0,0 | 3 | | |
| 49 | 10 | 0,0 | | 0,0 | | 1 | | |
| | 100 | 1,0 | | 0,0 | | 2 | | |
| | 1000 | 3,3 | 0,0 | 3,3 | 0,0 | 3 | | |
| 50 | 1000 | 3,3 | | 3,3 | 0,0 | 3 | | |
| | 1000 | 3,3 | 0,0 | 3,3 | 0,0 | 3 | | |
| | 10 | 1,1 | | 0,0 | | 0 | | |
| | 100 | 3,3 | | 3,3 | 0,0 | 3 | | |
| 51 | 1000 | 3,3 | 0,0 | 3,3 | 0,0 | 3 | | |
| | 10 | 2,1 | | 0,0 | | 2 | | |

TABLE II-continued

| Compound of Example No. | Appln. Rate ppm. | Mexican Bean Beetle Mortality Rating | Mexican Bean Beetle Feeding Rating | Southern Armyworm Mortality Rating | Southern Armyworm Feeding Rating | Two-spotted Spider Mite Mortality Rating | Housefly Mortality Rating Contact | Housefly Mortality Rating Knockdown |
|---|---|---|---|---|---|---|---|---|
|  | 100 | 3,3 | 1,1 | 3,3 | 0,0 | 3 | | |
| 52 | 1000 | 3,3 | 0,0 | 3,3 | 0,0 | 3 | | |
|  | 10 | 0,0 |  | 0,0 |  | 0 | | |
|  | 100 | 0,0 |  | 3,3 | 0,0 | 1 | | |
| 53 | 1000 | 3,2 | 1,1 | 3,3 | 0,0 | 3 | | |
|  | 10 | 0,0 |  | 0,0 |  | 1 | | |
|  | 100 | 0,0 |  | 2,2 | 1,1 | 2 | | |
| 54 | 1000 | 3,3 | 0,1 | 3,3 | 0,0 | 3 | | |
|  | 10 | 0,0 |  | 0,0 |  | 2 | | |
|  | 100 | 0,0 |  | 3,3 | 0,0 | 3 | | |
| 55 | 1000 | 3,3 | 1,0 | 3,3 | 0,0 | 3 | | |
|  | 10 | 0,0 |  | 0,0 |  | 2 | | |
|  | 100 | 0,0 |  | 3,3 | 0,0 | 3 | | |
| 56 | 1000 | 3,3 | 0,0 | 3,3 | 0,0 | 3 | | |
|  | 10 | 0,0 |  | 0,0 |  | 1 | | |
|  | 100 | 3,3 | 1,1 | 2,3 | 1,0 | 3 | | |

EXAMPLE 59: TWO-SPOTTED SPIDER MITE TEST

Numerous of the compounds to be employed in accordance with the present invention were evaluated for the control of the two-spotted spider mite (*Tetranychus urticae*) on plants of dry bean (variety Kentucky Wonder).

Each compound to be tested was formulated by dissolving it in a 1:1 mixture of acetone and anhydrous ethyl alcohol containing 23 grams of Toximul R and 13 grams of Toximul S per liter of solvent.

The testing procedure was as follows. Ten-day-old bean plants were trimmed until one stem with one leaf remained per plant, mite-infested leaves were placed on the trimmed plants and the mites were allowed to transfer for one to three days (generally two days). The infesting leaves were then removed and the newly infested plants were sprayed to the point of runoff with one of the test formulations and then maintained under favorable conditions. One to three days later (generally two days later) the degree of miticidal action was determined by counting the number of mites surviving in a total of eight microscope fields, about 6.28 sq. cm. of leaf area. Population counting was stopped as soon as 25 mites had been counted. Four replicates were conducted.

The following table records the results as the mean of the four replicates. Not all of the compounds were evaluated at the same time, but a solvent control (solvent concentration ranging from 4,000 ppm to 100,000 ppm) was included with each set of evaluations. Except where otherwise indicated, the mean solvent control number of mites was in each instance in excess of 25.

Plant injury ratings were generally made, on the following scale:
- 0 = no injury
- 1 = slight injury
- 2 = moderate injury
- 3 = severe injury Results are reported in the following table.

TABLE III
TWO-SPOTTED SPIDER MITE TEST

| Compound of Example No. | Dosage ppm. | Mean Number of Mites per 6.28 sq. cm. | Plant Injury Rating |
|---|---|---|---|
| 1 | 1000 | [2]/0.00 | 0 |
|  | 100 | 0.00 | 0 |
|  | 50 | 0.75 | 0 |
| 2 | 100 | 0.50 | 0 |
|  | 50 | 4.50 | 0 |
|  | 25 | 22.75 | 0 |
|  | 10 | 25.00 | 0 |
| 2 | 100 | 0.00 | 0 |
|  | 50 | 1.50 | 0 |
|  | 25 | 5.25 | 0 |
|  | 10 | 14.50 | 0 |
| 2 | 1000 | 0.00 | — |
|  | 100 | 1.00 | — |
|  | 10 | 24.50 | — |
| 2 | 100 | 2.25 | 0 |
|  | 50 | 5.50 | 0 |
|  | 10 | 11.75 | 0 |
| 2 | 100 | [5]/1.25 | 0 |
|  | 50 | 0.75 | 0 |
|  | 10 | 18.25 | 0 |
| 3 | 1000 | 0.00 | 0 |
|  | 100 | 0.00 | 0 |
|  | 50 | 0.25 | 0 |
| 3 | 100 | 0.00 | 0 |
|  | 50 | 0.25 | 0 |
|  | 25 | 2.25 | 0 |
|  | 10 | 9.00 | 0 |
| 3 | 100 | 1.25 | 0 |
|  | 50 | 5.50 | 0 |
|  | 25 | 17.50 | 0 |
|  | 10 | 23.50 | 0 |
| 3 | 100 | 0.00 | 0 |
|  | 50 | 1.50 | 0 |
|  | 25 | 12.50 | 0 |
|  | 10 | 25.00 | 0 |
| 3 | 100 | 0.00 | 0 |
|  | 50 | 1.00 | 0 |
|  | 25 | 1.75 | 0 |
|  | 10 | 3.75 | 0 |
| 3 | 1000 | [1]/0.00 | 0 |
|  | 100 | 0.00 | 0 |
|  | 50 | 0.00 | 0 |
| 3 | 100 | 3.00 | 0 |
|  | 50 | 2.00 | 0 |
|  | 25 | 14.50 | 0 |
|  | 10 | 23.50 | 0 |
| 3 | 1000 | 0.00 | 0 |
|  | 100 | 1.50 | 0 |
|  | 50 | 10.25 | 0 |
|  | 25 | 10.75 | 0 |
|  | 10 | 25.00 | 0 |

TABLE III-continued

TWO-SPOTTED SPIDER MITE TEST

| Compound of Example No. | Dosage ppm. | Mean Number of Mites per 6.28 sq. cm. | | Plant Injury Rating |
|---|---|---|---|---|
| 3 | 1000 | 0.00 | | — |
|  | 100 | 0.00 | | — |
|  | 10 | 8.00 | | — |
| 3 | 100 | 0.00 | | 0 |
|  | 50 | 0.00 | | 0 |
|  | 10 | 3.50 | | 0 |
| 3 | 100 | 5/0.25 | | 0 |
|  | 50 | 0.25 | | 0 |
|  | 10 | 8.25 | | 0 |
| 3 |  | nymphal and adult | larval |  |
|  | 1000 | 0.00 | 0.50 | 0 |
|  | 100 | 3.00 | 13.75 | 0 |
|  | 50 | 2.00 | 8.50 | 0 |
|  | 10 | 18.50 | 11.75 | 0 |
| 3 | 100 | 6/(18 hrs.) | 0.00 | — |
|  | 50 |  | 0.25 | — |
|  | 10 |  | 14.00 | — |
| 3 | 100 | 6/(24 hrs.) | 0.50 | — |
|  | 50 |  | 0.50 | — |
|  | 10 |  | 23.25 | — |
| 3 | 100 | 6/(42 hrs.) | 0.25 | — |
|  | 50 |  | 5.25 | — |
|  | 10 |  | 25.00 | — |
| 3 | 100 | 6/(48 hrs.) | 2.00 | — |
|  | 50 |  | 14.75 | — |
|  | 10 |  | 25.00 | — |
| 3 | 100 | 6/(66 hrs.) | 6.50 | — |
|  | 50 |  | 14.00 | — |
|  | 10 |  | 25.00 | — |
| 3 | 100 | 6/(72 hrs.) | 25.00 | — |
|  | 50 |  | 16.00 | — |
|  | 10 |  | 25.00 | — |
| 3 | 100 | 6/(90 hrs.) | 20.25 | — |
|  | 50 |  | 25.00 | — |
|  | 10 |  | 25.00 | — |
| 3 |  | treatment one day after infestation | treatment three days after infestation |  |
|  | 100 | 0.50 | 0.25 | — |
|  | 50 | 4.25 | 3.50 | — |
|  | 25 | 12.00 | 10.75 | — |
|  | 10 | 21.25 | 17.50 | — |
| 3 | 100 | 1.25 | | 0 |
|  | 50 | 18.50 | | 0 |
|  | 25 | 24.75 | | 0 |
|  | 10 | 25.00 | | 0 |
|  | 5 | 25.00 | | 0 |
|  | 1 | 25.00 | | 0 |
| 4 | 1000 | 0.00 | | 0 |
|  | 100 | 0.00 | | 0 |
|  | 50 | 0.00 | | 0 |
| 4 | 100 | 0.00 | | 0 |
|  | 50 | 0.25 | | 0 |
|  | 25 | 0.00 | | 0 |
|  | 10 | 2.00 | | 0 |
| 5 | 100 | 0.00 | | 0 |
|  | 50 | 0.50 | | 0 |
|  | 25 | 1.00 | | 0 |
|  | 10 | 11.25 | | 0 |
| 5 | 50 | 2.25 | | 0 |
|  | 25 | 10.00 | | 0 |
|  | 10 | 25.00 | | 0 |
| 5 | 1000 | 0.00 | | — |
|  | 100 | 0.00 | | — |
|  | 10 | 2.75 | | — |
| 5 | 1000 | 3/0.00 | | 0 |
|  | 100 | 0.25 | | 0 |
|  | 50 | 0.00 | | 0 |
| 5 | 100 | 0.00 | | 0 |
|  | 50 | 0.25 | | 0 |
|  | 25 | 2.25 | | 0 |
|  | 10 | 0.50 | | 0 |
| 5 | 100 | 0.25 | | 0 |
|  | 50 | 5.25 | | 0 |
|  | 25 | 4.25 | | 0 |
|  | 10 | 6.50 | | 0 |
| 5 |  | nymphal and adult | larval |  |
|  | 100 | 0.00 | 0.00 | 0 |
|  | 50 | 0.00 | 1.50 | 0 |
|  | 25 | 2.00 | 10.50 | 0 |
|  | 10 | 3.75 | 13.50 | 0 |
|  | 5 | 25.00 | 25.00 | 0 |
|  | 1 | 25.00 | 25.00 | 0 |
| 5 | 1000 | 0.00 | 0.00 | 0 |
|  | 100 | 0.00 | 0.00 | 0 |
|  | 50 | 0.00 | 0.75 | 0 |
|  | 10 | 1.25 | 7.00 | 0 |
| 5 | 100 | 6/(18 hrs.) | 0.00 | — |
|  | 50 |  | 0.25 | — |
|  | 10 |  | 14.00 | — |
| 5 | 100 | 6/(24 hrs.) | 0.25 | — |
|  | 50 |  | 0.00 | — |
|  | 10 |  | 7.75 | — |
| 5 | 100 | 6/(42 hrs.) | 0.00 | — |
|  | 50 |  | 0.00 | — |
|  | 10 |  | 15.50 | — |
| 5 | 100 | 6/(48 hrs.) | 0.25 | — |
|  | 50 |  | 0.75 | — |
|  | 10 |  | 13.25 | — |
| 5 | 100 | 6/(66 hrs.) | 6.25 | 0 |
|  | 50 |  | 5.75 | 0 |
|  | 10 |  | 2.25 | 0 |
| 5 | 100 | 6/(72 hrs.) | 6.75 | — |
|  | 50 |  | 10.50 | — |
|  | 10 |  | 12.25 | — |
| 5 | 100 | 6/(90 hrs.) | 10.25 | — |
|  | 50 |  | 20.00 | — |
|  | 10 |  | 16.00 | — |
| 5 |  | treatment one day after infestation | treatment three days after infestation |  |
|  | 50 | 3.57 | 0.25 | — |
|  | 25 | 4.50 | 1.75 | — |
|  | 10 | 22.50 | 2.25 | — |
| 6 | 4000 | 1.50 | | 0 |
|  | 2000 | 2.00 | | 0 |
|  | 1000 | 14.50 | | 0 |
|  | 100 | 18.50 | | 0 |
|  | 50 | 21.00 | | 0 |
| 6 | 4000 | 5.25 | | 0 |
|  | 2000 | 5.25 | | 0 |
|  | 1000 | 3.25 | | 0 |
|  | 100 | 13.00 | | 0 |
|  | 50 | 20.25 | | 0 |
| 8 | 1000 | 0.00 | | 0 |
|  | 100 | 0.25 | | 0 |
|  | 50 | 0.50 | | 0 |
| 10 | 1000 | 1/4.25 | | 0 |
|  | 100 | 25.00 | | 0 |
|  | 50 | 25.00 | | 0 |
| 11 | 100 | 0.75 | | 0 |
|  | 50 | 3.25 | | 0 |
|  | 25 | 5.25 | | 0 |
|  | 10 | 14.00 | | 0 |
| 12 | 1000 | 14.50 | | 0 |

TABLE III-continued

TWO-SPOTTED SPIDER MITE TEST

| Compound of Example No. | Dosage ppm. | Mean Number of Mites per 6.28 sq. cm. | Plant Injury Rating |
|---|---|---|---|
| | 100 | 25.00 | 0 |
| | 50 | 25.00 | 0 |
| | 25 | 25.00 | 0 |
| | 10 | 25.00 | 0 |
| 13 | 1000 | 0.00 | 0 |
| | 100 | 25.00 | 0 |
| | 50 | 25.00 | 0 |
| 14 | 1000 | 2/15.75 | 0 |
| | 100 | 25.00 | 0 |
| | 50 | 25.00 | 0 |
| 15 | 1000 | 13.50 | 0 |
| | 100 | 23.75 | 0 |
| | 50 | 25.00 | 0 |
| 15 | 4000 | 14.25 | 0 |
| | 2000 | 24.75 | 0 |
| | 1000 | 22.75 | 0 |
| 16 | 1000 | 0.00 | 0 |
| | 100 | 0.00 | 0 |
| | 50 | 1.75 | 0 |
| 16 | 100 | 0.00 | 0 |
| | 50 | 3.00 | 0 |
| | 25 | 5.50 | 0 |
| | 10 | 8.00 | 0 |
| 17 | 1000 | 0.50 | 0 |
| | 100 | 25.00 | 0 |
| | 50 | 18.75 | 0 |
| 18 | 1000 | 1/0.50 | 0 |
| | 100 | 18.00 | 0 |
| | 50 | 23.00 | 0 |
| 19 | 1000 | 2.00 | 0 |
| | 100 | 15.25 | 0 |
| | 50 | 23.50 | 0 |
| 20 | 100 | 0.00 | 0 |
| | 50 | 0.00 | 0 |
| | 25 | 4.25 | 0 |
| | 10 | 9.25 | 0 |
| 20 | 100 | 10.25 | 0 |
| | 50 | 3.00 | 0 |
| | 25 | 22.00 | 0 |
| | 10 | 19.50 | 0 |
| 20 | 1000 | 4.00 | 0 |
| | 100 | 0.00 | 0 |
| | 50 | 0.25 | 0 |
| 20 | 1000 | 2.00 | 0 |
| | 100 | 7.25 | 0 |
| | 50 | 23.50 | 0 |
| 20 | 1000 | 1.75 | 0 |
| | 100 | 0.50 | 0 |
| | 50 | 1.25 | 0 |
| 20 | 1000 | 0.50 | — |
| | 100 | 0.00 | — |
| | 10 | 18.00 | — |
| 20 | 100 | 1.25 | 0 |
| | 50 | 0.25 | 0 |
| | 10 | 4.50 | 0 |
| 20 | 100 | 5/0.00 | 0 |
| | 50 | 0.75 | 0 |
| | 10 | 1.00 | 0 |
| 21 | 1000 | 0.25 | 0 |
| | 100 | 1.75 | 0 |
| | 50 | 6.75 | 0 |
| 22 | 1000 | 18.50 | 0 |
| | 100 | 25.00 | 0 |
| | 50 | 25.00 | 0 |
| 23 | 1000 | 0.00 | 0 |
| | 100 | 1.00 | 0 |
| | 50 | 7.25 | 0 |
| 23 | 1000 | 0.00 | 0 |
| | 100 | 0.00 | 0 |
| | 50 | 0.00 | 0 |
| 23 | 100 | 2.25 | 0 |
| | 50 | 9.00 | 0 |
| | 25 | 5.00 | 0 |
| | 10 | 21.25 | 0 |
| 23 | 1000 | 0.00 | 0 |
| | 100 | 0.00 | 0 |
| | 50 | 0.00 | 0 |
| 23 | 1000 | 0.00 | 0 |
| | 100 | 1.00 | 0 |
| | 50 | 7.25 | 0 |
| 24 | 1000 | 0.00 | 0 |
| | 100 | 0.25 | 0 |
| | 50 | 0.00 | 0 |
| 25 | 100 | 0.00 | 0 |
| | 50 | 1.00 | 0 |
| | 25 | 4.00 | 0 |
| | 10 | 6.50 | 0 |
| 25 | 1000 | 2.25 | 0 |
| | 100 | 7.00 | 0 |
| | 50 | 1.75 | 0 |
| 25 | 1000 | 0.00 | 0 |
| | 100 | 1.25 | 0 |
| | 50 | 2.50 | 0 |
| 25 | 100 | 10.75 | 0 |
| | 50 | 9.00 | 0 |
| | 25 | 6.25 | 0 |
| | 10 | 21.25 | 0 |
| 25 | 1000 | 0.75 | — |
| | 100 | 0.25 | — |
| | 10 | 20.25 | — |
| 25 | 100 | 0.75 | 0 |
| | 50 | 1.00 | 0 |
| | 10 | 14.00 | 0 |
| 25 | 100 | 5/0.00 | 0 |
| | 50 | 1.75 | 0 |
| | 10 | 15.25 | 0 |
| 26 | 1000 | 0.00 | 0 |
| | 100 | 4.50 | 0 |
| | 50 | 7.75 | 0 |
| 26 | 1000 | 0.00 | 0 |
| | 100 | 0.25 | 0 |
| | 50 | 1.75 | 0 |
| 27 | 1000 | 0.75 | 0 |
| | 100 | 17.00 | 0 |
| | 50 | 17.25 | 0 |
| 28 | 2000 | 0.00 | — |
| | 500 | 0.25 | — |
| | 100 | 3.5 | — |
| | 50 | 11.25 | — |
| | 25 | 17.75 | — |
| 29 | 100 | 0.00 | 0 |
| | 50 | 0.25 | 0 |
| | 25 | 2.50 | 0 |
| | 10 | 8.25 | 0 |
| 29 | 1000 | 0.00 | 0 |
| | 100 | 0.25 | 0 |
| | 50 | 1.25 | 0 |
| 29 | 100 | 1.25 | 0 |
| | 50 | 2.25 | 0 |
| | 25 | 375 | 0 |
| | 10 | 17.75 | 0 |
| 30 | 4000 | 21.75 | 0 |
| | 2000 | 22.75 | 0 |
| | 1000 | 23.50 | 0 |
| 30 | 1000 | 0.25 | 0 |
| | 100 | 3.50 | 0 |
| | 50 | 7.50 | 0 |
| 31 | 100 | 0.00 | 0 |
| | 50 | 0.25 | 0 |
| | 25 | 1.25 | 0 |
| | 10 | 8.00 | 0 |
| 31 | 1000 | 0.00 | 0 |
| | 100 | 0.25 | 0 |
| | 50 | 0.25 | 0 |
| 31 | 1000 | 0.00 | 0 |
| | 100 | 0.00 | 0 |
| | 50 | 0.25 | 0 |
| 31 | 1000 | 0.00 | — |
| | 100 | 0.50 | — |
| | 10 | 9.50 | — |
| 31 | 100 | 0.25 | 0 |
| | 50 | 1.25 | 0 |
| | 10 | 3.25 | 0 |
| 31 | 100 | 5/0.00 | 0 |

TABLE III-continued
TWO-SPOTTED SPIDER MITE TEST

| Compound of Example No. | Dosage ppm. | Mean Number of Mites per 6.28 sq. cm. | Plant Injury Rating |
|---|---|---|---|
|  | 50 | 0.25 | 0 |
|  | 10 | 7.75 | 0 |
| 32 | 1000 | 1/1.50 | 0 |
|  | 100 | 2.00 | 0 |
|  | 50 | 9.00 | 0 |
| 33 | 1000 | 24.00 | 0 |
|  | 100 | 25.00 | 0 |
|  | 50 | 25.00 | 0 |
| 33 | 1000 | 9.25 | 0 |
|  | 100 | 21.00 | 0 |
|  | 50 | 23.50 | 0 |
| 34 | 1000 | 1.00 | 0 |
|  | 100 | 19.50 | 0 |
|  | 50 | 19.50 | 0 |
| 34 | 1000 | 4.50 | 0 |
|  | 100 | 10.50 | 0 |
|  | 50 | 11.25 | 0 |
| 35 | 1000 | 2/1.25 | 0 |
|  | 100 | 18.50 | 0 |
|  | 50 | 22.25 | 0 |
| 36 | 100 | 0.00 | 0 |
|  | 50 | 0.75 | 0 |
|  | 25 | 2.25 | 0 |
|  | 10 | 14.75 | 0 |
| 37 | 1000 | 0.50 | 0 |
|  | 100 | 8.25 | 0 |
|  | 50 | 16.25 | 0 |
| 38 | 1000 | 0.00 | 0 |
|  | 100 | 3.50 | 0 |
|  | 50 | 20.50 | 0 |
| 39 | 1000 | 1.00 | 0 |
|  | 100 | 4.75 | 0 |
|  | 50 | 11.75 | 0 |
| 40 | 1000 | 18.25 | 0 |
|  | 100 | 25.00 | 0 |
|  | 50 | 22.50 | 0 |
| 40 | 4000 | 2.25 | 0 |
|  | 2000 | 10.25 | 0 |
|  | 1000 | 3.00 | 0 |
| 41 | 1000 | 0.00 | 0 |
|  | 100 | 0.25 | 0 |
|  | 50 | 9.50 | 0 |
| 41 | 100 | 14.25 | 0 |
|  | 50 | 18.00 | 0 |
|  | 25 | 25.00 | 0 |
|  | 10 | 25.00 | 0 |
| 42 | 1000 | 3/22.00 | 0 |
|  | 100 | 25.00 | 0 |
|  | 50 | 25.00 | 0 |
| 42 | 1000 | 12.00 | 0 |
|  | 100 | 23.50 | 0 |
|  | 50 | 25.00 | 0 |
| 43 | 1000 | 0.00 | 0 |
|  | 100 | 12.75 | 0 |
|  | 50 | 21.75 | 0 |
| 44 | 1000 | 0.00 | 0 |
|  | 100 | 7.25 | 0 |
|  | 50 | 18.50 | 0 |
| 45 | 1000 | 0.00 | 0 |
|  | 100 | 0.50 | 0 |
|  | 50 | 3.25 | 0 |
| 45 | 1000 | 14.25 | — |
|  | 100 | 22.00 | — |
|  | 50 | 24.50 | — |
| 45 | 100 | 11.00 | 0 |
|  | 50 | 20.00 | 0 |
|  | 25 | 20.00 | 0 |
|  | 10 | 23.50 | 0 |
| 46 | | nymphal and adult / larval | |
|  | 1000 | 1.75 / 10.50 | 1.0 |
|  | 100 | 0.00 / 6.25 | 0 |
|  | 50 | 0.75 / 19.00 | 0 |
|  | 25 | 2.00 / 14.00 | 0 |
|  | 10 | 2.25 / 12.75 | 0 |
| 47 | 1000 | 0.00 | 0.75 |
|  | 100 | 25.00 | 0 |
|  | 50 | 25.00 | 0 |
| 48 | 100 | 0.75 | 0 |
|  | 50 | 20.50 | 0 |
|  | 25 | 17.50 | 0 |
|  | 10 | 19.75 | 0 |
| 48 | 1000 | 0.00 | 0 |
|  | 100 | 13.50 | 0 |
|  | 50 | 11.50 | 0 |
|  | 25 | 24.75 | 0 |
|  | 10 | 25.00 | 0 |
| 48 | | treatment one day after infestation / treatment three days after infestation | |
|  | 1000 | 0.25 / 0.00 | — |
|  | 100 | 0.00 / 0.00 | — |
|  | 50 | 0.50 / 0.00 | — |
|  | 25 | 1.75 / 0.00 | — |
|  | 10 | 2.00 / 0.00 | — |
| 49 | 4000 | 0.75 | 0 |
|  | 2000 | 0.00 | 0 |
|  | 1000 | 1.75 | 0 |
|  | 100 | 8.75 | 0 |
|  | 50 | 19.00 | 0 |
| 49 | 4000 | 1.25 | 0 |
|  | 2000 | 4.25 | 0 |
|  | 1000 | 4.50 | 0 |
|  | 100 | 13.25 | 0 |
|  | 50 | 20.25 | 0 |
| 50 | 1000 | 1.00 | 0 |
|  | 100 | 0.50 | 0 |
|  | 50 | 11.50 | 0 |
| 51 | 1000 | 0.00 | 0 |
|  | 100 | 0.00 | 0 |
|  | 50 | 0.00 | 0 |
| 52 | 1000 | 0.25 | 0 |
|  | 100 | 20.75 | 0 |
|  | 50 | 25.00 | 0 |
| 53 | 1000 | 0.00 | 0 |
|  | 100 | 7.75 | 0 |
|  | 50 | 23.00 | 0 |
| 54 | 1000 | 0.00 | 2.75 |
|  | 100 | 1.75 | 0 |
|  | 50 | 17.75 | 0 |
| 55 | 1000 | 0.00 | 0 |
|  | 100 | 3.00 | 0 |
|  | 50 | 9.25 | 0 |
| 56 | 1000 | 0.00 | 0 |
|  | 100 | 1.25 | 0 |
|  | 50 | 9.25 | 0 |

1/Control plants for this test (solvent conc. = 40,000 ppm) showed a mean of only 22.25 mites.
2/Control plants for this test (solvent conc. = 40,000 ppm) showed a mean of only 19.25 mites.
3/Control plants for this test (solvent conc. = 70,000 ppm) showed a mean of only 19.50 mites.
4/Control plants for this test (solvent conc. = 100,000 ppm) showed a mean of only 21.75 mites.
5/Formulated as an emulsifiable concentrate as described in Example 55; carried out at same time as test immediately preceding in this table for a comparison of formulation effect.
6/Readings were made at 18 hours, 24 hours, 42 hours, 48 hours, 66 hours, 72 hours, and 90 hours after treatment of the plants.

EXAMPLE 60: RESISTANT TWO-SPOTTED SPIDER MITE TEST

A few of the compounds to be employed in accordance with the present invention were simultaneously evaluated for the control of two strains of two-spotted spider mites, a first strain of normal susceptibility (the same strain as used in the preceding experiments), and a second strain known to be resistant to standard organophosphate and carbamate toxicants. The evaluation was carried out as set forth in the test procedures described immediately preceding. The test results were as set forth in the following table.

TABLE IV
RESISTANT TWO-SPOTTED SPIDER MITE TEST

| Compound of Example No. | Dosage ppm. | Mean Number of Normal Mites per 6.28 sq. cm. | of Resistant Mites per 6.28 sq. cm. |
|---|---|---|---|
| Test 1[1] | | | |
| 2 | 1000 | 0.00 | 25.00 |
| | 100 | 0.00 | 25.00 |
| | 50 | 0.00 | 25.00 |
| 25 | 1000 | 0.25 | 9.75 |
| | 100 | 0.50 | 15.25 |
| | 50 | 0.50 | 25.00 |
| 20 | 1000 | 12.25 | 25.00 |
| | 100 | 4.50 | 25.00 |
| | 50 | 14.50 | 25.00 |
| 31 | 1000 | 0.00 | 8.50 |
| | 100 | 0.00 | 24.50 |
| | 50 | 0.00 | 25.00 |
| Test 2[2] | | | |
| 3 | 1000 | 0.75 | 0.25 |
| | 100 | 17.75 | 25.00 |
| | 10 | 25.00 | 25.00 |
| 5 | 1000 | 0.00 | 0.50 |
| | 100 | 8.50 | 4.50 |
| | 10 | 25.00 | 25.00 |
| 25 | 1000 | 15.50 | 15.75 |
| | 100 | 24.50 | 25.00 |
| | 10 | 25.00 | 25.00 |
| 2 | 1000 | 2.75 | 8.25 |
| | 100 | 19.50 | 25.00 |
| | 10 | 25.00 | 25.00 |
| 20 | 1000 | 6.25 | 25.00 |
| | 100 | 1.50 | 23.25 |
| | 10 | 25.00 | 25.00 |
| 31 | 1000 | 0.00 | 0.25 |
| | 100 | 2.75 | 25.00 |
| | 10 | 25.00 | 25.00 |
| Test 3[3] | | | |
| 3 | 1000 | 0.00 | 0.00 |
| | 100 | 0.00 | 0.00 |
| | 10 | 10.25 | 2.50 |
| Test 4[4] | | | |
| 3 | 1000 | 0.00 | 0.00 |
| | 100 | 0.00 | 0.00 |
| | 10 | 0.00 | 0.25 |
| Test 5[5] | | | |
| 3 | 1000 | 0.00 | 0.00 |
| | 100 | 0.00 | 0.00 |
| | 50 | 0.00 | 2.50 |

[1]Control plants for this test (solvent conc. = 70,000 ppm.) showed a mean of 25.00 normal mites and a mean of 23.75 resistant mites. No phytotoxicity was observed in either control or in any of the treatments.
[2]Control plants for this test (solvent conc. = 50,000 ppm.) showed a mean of 25.00 both normal and resistant mites. Phytotoxicity was not evaluated.
[3]Control plants for this test (solvent conc. = 40,000 ppm.) showed a mean of 25.00 both normal and resistant mites. No phytotoxicity was observed.
[4]Control plants for this test (solvent conc. = 50,000 ppm.) showed a mean of 25.00 both normal and resistant mites. Phytotoxicity was not evaluated.
[5]Control plants for this test (solvent conc. = 50,000 ppm.) showed a mean of 25.00 both normal and resistant mites. Phytotoxicity was not evaluated.

EXAMPLE 61: TWO-SPOTTED SPIDER MITE OVICIDE TEST

Two of the compounds to be employed in accordance with the present invention were evaluated as ovicides. The evaluation was generally carried out as reported in Example 52, but with certain modifications.

Plictran, which is non-ovicidal, was employed as a reference. As soon as the Plictran reference plants showed newly hatched mites (about 4 days after treatment), leaves were detached and examined under a microscope. Larval mites and unhatched eggs were counted in four microscope fields (about 3.14 sq. cm. of leaf area). The percent egg hatch was calculated as the number of larvae divided by the number of larvae plus unhatched eggs, multiplied by 100. The results were as set forth in the following table.

TABLE V
TWO SPOTTED SPIDER MITE OVICIDE TEST

| | Compound of Example No. | Dosage | Percent Egg Hatch |
|---|---|---|---|
| Test 1 | 3 | 500 | 0.00 |
| | | 100 | 94.50 |
| | 31 | 1000 | 0.00 |
| | | 500 | 0.00 |
| | | 100 | 2.25 |
| | Plictran | 10 | 82.50 |
| Test 2 | 3 | 500 | 6.75 |
| | | 100 | 92.49 |
| | | 50 | 91.56 |
| | 31 | 500 | 0.00 |
| | | 100 | 92.92 |
| | | 50 | 97.43 |
| | Plictran | 10 | 87.76 |
| Test 3 | 3 | 500 | 2.10 |
| | | 400 | 0.87 |
| | | 300 | 10.26 |
| | | 200 | 45.50 |
| | | 100 | 89.28 |
| | 31 | 500 | 0.00 |
| | | 400 | 0.00 |
| | | 300 | 0.00 |
| | | 200 | 0.00 |
| | | 100 | 1.65 |
| | Plictran | 10 | 93.47 |

EXAMPLE 62: FORMULATIONS

Various of the compounds to be employed in accordance with the present invention were formulated as emulsifiable concentrates and/or wettable powders. The composition of the formulations was as follows:

| component | percent |
|---|---|
| Emulsifiable Concentrate (2 lbs./gal., hereinafter "2EC") | |
| N—methyl-2,4-difluoro-2',4'-dinitro-6'-(trifluoromethyl)diphenylamine | 25.0 |
| Toximul D | 5.0 |
| Toximul H | 5.0 |
| Dowanol EM | 20.0 |
| Xylene | 45.0 |
| Wettable Powder (50%, hereinafter "50WP") | |
| N—methyl-2,4-difluoro-2',4'-dinitro-6'-(trifluoromethyl)diphenylamine | 51.5 |
| Stepanol ME | 5.0 |
| Polyfon O | 5.0 |
| Zeolex-7 | 5.0 |
| Bardens Clay | 33.5 |
| Emulsifiable Concentrate (1 lb./gal., hereinafter "1EC") | |
| N—methyl-4-fluoro-2',4'-dinitro-6'-(trifluoromethyl)diphenylamine | 12.5 |
| Toximul D | 5.0 |
| Toximul H | 5.0 |
| Xylene | 77.5 |
| N—methyl-3-(trifluoromethyl)-2',4'-dinitro-6'-(trifluoromethyl)diphenylamine | 12.5 |
| Toximul D | 5.0 |
| Toximul H | 5.0 |
| Xylene | 77.5 |
| Emulsifiable Concentrate (0.5 lb./gal., hereinafter "0.5EC") | |
| N—methyl-4-bromo-2',4'-dinitro-6'-(trifluoromethyl)diphenylamine | 6.5 |
| Toximul D | 5.0 |
| Toximul H | 5.0 |

-continued

| component | percent |
|---|---|
| Dowanol EM | 20.0 |
| Xylene | 63.5 |

Emulsifiable Concentrate (1 lb./gal., hereinafter "1EC")

| | |
|---|---|
| N—methyl-4-chloro-2',4'-dinitro-6'-(trifluoromethyl)diphenylamine | 12.5 |
| Toximul D | 5.0 |
| Toximul H | 5.0 |
| Acetophenone | 77.5 |

Emulsifiable Concentrate (1.5 lb./gal., hereinafter "1.5EC")

| | |
|---|---|
| N—methyl-2,4-difluoro-2',4'-dinitro-6'-(trifluoromethyl)-diphenylamine | 19.0 |
| Toximul D | 2.5 |
| Toximul H | 2.5 |
| Dowanol EM | 22.0 |
| Xylene | 54.0 |
| N—methyl-3-(trifluoromethyl)-2',4'-dinitro-6'-(trifluoromethyl)diphenylamine | 19.0 |
| Toximul D | 2.5 |
| Toximul H | 2.5 |
| Dowanol EM | 22.0 |
| Xylene | 54.0 |

Each of Toximul D and H is a sulfonate-nonionic blend of emulsifiers produced by Stepan Chemical Co. Dowanol EM is a brand of ethylene glycol methyl ether sold by Dow Chemical Co. Stepanol ME is a brand of sodium lauryl sulfate sold by Stepan Chemical Co. Polyfon O is a dispersant comprising sugar free, sodium based sulfonates of Kraft lignin; it is sold by Westvaco Corporation, Polychemicals Dept. Zeolex-7 is a hydrated sodium silico aluminate of ultrafine particle size, sold by J. M. Huber Corp.

EXAMPLE 63: TWO SPOTTED SPIDER MITE, GREEN PEACH APHID, AND LYGUS BUG

N-Methyl-2,4-difluoro-2',4'-dinitro-6-(trifluoromethyl)diphenylamine (2EC as described in Example 62) was foliar applied under laboratory conditions to detached plant leaves at rates of 1 and 2 lb/100 gallons (1200 and 2400 ppm, respectively) of spray concentration using a $CO_2$ hand-held sprayer. A single application was made to detached soybean leaves infested with two-spotted spider mite (*Tetranychus urticae*), mustard leaves infested with green peach aphid (*Myzus persicae*) and mungbean leaves infested with lygus bugs (*Lygus hyesperus*). After treatment, the mustard and soybean leaves were placed in petri dish moist chambers and the mungbean leaves were placed in small plastic containers covered with cheesecloth.

Live insect counts taken one day after treatment indicated that the test compound at 1 and 2 lb/100 gallons provided 55 and 74 percent control of lygus bug and 86 and 95 percent control of green peach aphid, respectively. Greater than 90 percent control of the two-spotted spider mite was achieved with both rates of compound.

EXAMPLE 64: IMPORTED CABBAGEWORM, DIAMONDBACK MOTH, CABBAGE LOOPER, BEET ARMYWORM, AND GRAPE SKELETONIZER

N-Methyl-2,4-difluoro-2',4'-dinitro-6'-(trifluoromethyl)diphenylamine (2EC as described in Example 62) was foliar applied under laboratory conditions to detached plant leaves at the rate of 1 lb/100 gallons of spray solution (1200 ppm) using a hand-held sprayer with compressed air as the propellant. A single application was made to five (3rd to 5th instar) larvae of the following insect species: imported cabbageworm (*Pieris rapae*) on a broccoli leaf; diamondback moth (*Plutella xylostella*) on a broccoli leaf; cabbage looper (*Trichoplusia ni*) on a broccoli leaf; beet armyworm (*Spodoptera exigua*) on a sugar beet leaf; and grapeleaf skeletonizer (*Harrisina brillians*) on a grape leaf. After treatment, the leaves with the insect larvae were placed in petri dish moist chambers for further observation.

Live insect counts taken two days after treatment indicated that the test compound killed 94 percent of the grapeleaf skeletonizer larvae, 53 percent of the imported cabbageworm larvae, 85 percent of the diamondback moth larvae, 100 percent of the beet armyworm larvae, and 77 percent of the cabbage looper larvae.

EXAMPLE 65: PACIFIC SPIDER MITE

N-Methyl-2,4-difluoro-2',4'-dinitro-6'-(trifluoromethyl)diphenylamine (2EC as described in Example 62) was foliar applied under laboratory conditions to detached Thompson seedless grape leaves at rates of 0.25, 0.5 and 1 lb/100 gallons of spray solution. Comite 6.75EC at 3.4 lb/100 gallons and Fundal 4EC at 2 lb/100 gallons of spray solution were included as references.

Four leaves per treatment infested with Pacific spider mites (*Tetranychus pacificus*) were sprayed with a hand-held single nozzle boom. The treated leaves were placed in petri plates with the mite-infested lower leaf surface exposed outward and stored in the greenhouse under a constant temperature of 78° F. and 24-hour light. The leaves were evaluated one day after treatment for miticide activity and four days after treatment for ovicide activity under a dissecting microscope.

The test compound was observed to provide 95 to 100 percent control of the Pacific spider mite at all rates evaluated. The reference compounds of Comite and Fundal provided 71 and 75 percent control, respectively. All the chemical treatments prevented egg hatch four days after treatment.

EXAMPLE 66: TWO SPOTTED SPIDER MITE, FIELD TEST ON ALMOND

N-Methyl-2,4-difluoro-2',4'-dinitro-6'-(trifluoromethyl)diphenylamine (2EC as described in Example 62) was foliar applied at rates of 0.5, 1, and 2 lb/100 gallons spray solution to individual branches of nonpariel almond trees infested with two-spotted spider mites (*Tetranychus urticae*). Kelthane MF 4EC at the rate of 2 lb/100 gallons was also included. A single application was made with a $CO_2$ hand-held sprayer with a single nozzle boom until the entire leaf surfaces were wet. Two days after application, ten leaves per treatment were examined under a dissecting microscope and the total number of mites recorded.

Two-spotted spider mite counts of adults and nymphs taken two days post treatment showed greater than 90 percent control at all rates with the test compound. The reference treatment of Kelthane at 2 lb/100 gallon was observed to provide 80 percent control. No crop injury evaluations were taken due to the initiation of leaf senescence.

EXAMPLE 67: CABBAGE LOOPER, DIAMONDBACK MOTH, AND IMPORTED CABBAGEWORM, FIELD TEST ON BROCCOLI

N-Methyl-2,4-difluoro-2',4'-dinitro-6'-(trifluoromethyl)diphenylamine (2EC as described in Example 62) was foliar applied at rates of 0, 5 and 1.0 lb./acre to broccoli for control of cabbage looper (*Trichoplusia ni*), diamondback moth (*Plutella xylostella*), and imported cabbageworm (*Pieris rapae*). Applications were made every six days for a total of three applications. A Hagie high-clearance sprayer using compressed air as propellant to feed a 6-nozzle boom was utilized in all treatments. Individual plots consisted of two rows, 20 feet long, with each treatment replicated four times. Data on crop injury, insect injury, and various insect counts were taken after each application.

The test compound at 0.5 and 1 lb./acre provided 40 and 26 percent insect injury, respectively, while the reference treatments of Dimilin 25W at 0.5 lb/acre and Lannate 1.8L at 0.5 lb/acre were 39 and 8 percent, respectively. Unacceptable control of cabbage looper was noted in all treatments. The test compound provided less than 70 percent control of the three Lepidoptera species. Moderate crop injury (crinkled and necrotic leaf tissue) was observed with the test compound.

EXAMPLE 68: TWO SPOTTED SPIDER MITE, FIELD TEST ON SOYBEANS

N-Methyl-2,4-difluoro-2',4'-dinitro-6'-(trifluoromethyl)diphenylamine (2EC and 50WP as described in Example 62) was foliar applied to soybeans at rates of 0.5, 1, and 2 lb/acre in a spray volume of 100 gallons/acre. A Hagie high-clearance sprayer using compressed air as propellant to feed a 6-nozzle boom was utilized in all treatments. Plot size consisted of two soybean rows, 20 feet long, with each treatment replicated four times. Comite 6.75EC at 3.4 lb/100 gallons, Kelthane 4EC at 3 lb/100 gallons, and Fundal 4EC at 3 lb/100 gallons were included as reference treatments. Mite counts were made on each soybean leaflet from 5 to 10 trifoliate leaves taken at random from each plot. Each leaflet was placed under a dissecting microscope and the total number of living mites observed in a 0.5" field at the base of the leaflet adjacent to the midrib was recorded. Pretreatment evaluations indicated two-spotted spider mite (*Tetranychus urticae*) populations ranging from 5 to 20 mites per 0.5" field under a dissecting microscope.

Seven days after treatment, the test compound at 0.5 to 2 lb/acre was providing 75 to 99 percent control of two-spotted spider mites for both formulations. The test compound was equally effective on the nymphs and adult mites. The reference treatments of Comite 6.75EC at 3.4 lb/acre, Kelthane 3EC at 3 lb/acre, and Fundal 3EC at 3 lb/acre resulted in 88, 92, and 77 percent mite control, respectively. The population of predacious mites (Typhlodromus spp.) was reduced 20 to 50 percent less in the test compound treatments as compared to the standard reference treatments. Very slight crop injury (<8%) to the soybeans was noted with the 1 and 2 lb/acre rates of the test compound.

EXAMPLE 69: PACIFIC SPIDER MITE AND TWO SPOTTED SPIDER MITE

N-Methyl-2,4-difluoro-2',4'-dinitro-6'-(trifluoromethyl)diphenylamine (2EC as described in Example 62) was foliar applied under laboratory conditions to detached cotton leaves infested with spider mites at rates of 0.25, 0.5, 1, and 2 lb/100 gallons. Comite 6.75EC at 3.4 lb/100 gallons and Kelthane 4EC at 2 lb/100 gallons were included as references. Four leaves per treatment were sprayed with a hand-held single nozzle boom until completely wet. The treated leaves were placed in petri dishes with the mite-infested lower leaf surface exposed outward and stored in the greenhouse under a constant 78° F. temperature and 24-hour light. Four days after treatment, the total number of live and dead mites per leaf were counted under a dissecting microscope. Mite population consisted of Pacific spider mite (*Tetranychus pacificus*) and two-spotted spider mite (*Tetranychus urticae*).

The test compound at 0.25 to 2 lb/100 gallons and Comite 6.75EC at 3.4 lb/100 gallons provided 100 percent control of the mite species. Kelthane 4EC at 2 lb/100 gallons resulted in 94 percent control.

EXAMPLE 70: TWO SPOTTED SPIDER MITE, FIELD TEST ON MUNG BEANS

N-Methyl-2,4-difluoro-2',4'-dinitro-6'-(trifluoromethyl)diphenylamine (2EC as described in Example 62) was foliar applied to mung beans at rates of 0.5, 1, 2 and 2.5 lb/acre (1 to 5 lb/100 gallons) in a spray volume of 50 gallons per acre. Comite 6.75EC was included at 1.7 lb/acre as a positive miticide reference standard. A Hagie high-clearance sprayer utilizing compressed air as the propellant and feeding a six-nozzle boom was used in all applications. Each plot consisted of two rows of mung beans 20 feet long, with each treatment replicated four times. Mite counts were made on the uppermost leaflet from each of five trifoliate leaves taken at random from each plot. Each leaflet was placed under a dissecting microscope and the total number of living mites observed in a 0.5" field adjacent to the midrib was recorded. Pretreatment evaluations indicated two-spotted spider mite (*Tetranychus urticae*) populations ranging from 0 to 28 mites per 0.5" field under a dissecting microscope. Mite population pressure was high in this experiment since mite colonies built up rapidly on untreated buffer plants adjacent to treated rows.

Two days following treatment, the test compound at 0.5 to 2.5 lb/acre gave 80 to 93 percent mite control with only slight injury to mung beans at 1 lb/acre and above. Seven days following the first application, the test compound continued to provide acceptable control of adult mites at all rates; however, control of nymph populations was not satisfactory. Two days following a second application, the test compound at 0.5 to 2 lb/acre gave 74 to 96 percent control of two-spotted spider mites with only slight phytotoxicity. Comite 6.75EC at 1.7 lb/acre failed to provide acceptable mite control following the first application and only 60 to 70 percent control was obtained following a second application. This poor performance of the reference miticide was thought to be the result of extremely high mite populations in this experiment.

EXAMPLE 71: TWO SPOTTED SPIDER MITE, FIELD TEST ON COTTON

N-Methyl-2,4-difluoro-2',4'-dinitro-6'-(trifluoromethyl)diphenylamine (2EC as described in Example 62) was foliar applied to short staple cotton during the early-bloom stage at rates of 1 to 3 lb/100 gallons of water. Comite 6.7EC and Galecron 95W were applied as reference miticides at 3.4 and 0.5 lb/100 gallons, respectively. Applications were made using a $CO_2$ backpack sprayer fitted with a single nozzle covering all leaf surfaces to the point of runoff. One application was made on the cotton with four, single-plant replicates per treatment. Mite counts were made on three leaves from each plant recording the total number of living mites observed in a 0.5" microscope field adjacent to the midrib. Pretreatment observations revealed that the two-spotted spider mite (*Tetranychus urticae*) was present on the foliage at a level sufficient to cause economic injury on cotton.

Two days following application the test compound at 1 to 3 lb/100 gallons gave 85 to 100 percent control of two-spotted spider mite with no crop injury. The Comite and Galecron treatments also provided acceptable mite control. Five days after application the test compound at 1.5 to 3 lb/100 gallons and the Comite and Galecron treatments continued to provide satisfactory mite control.

EXAMPLE 72: TWO SPOTTED SPIDER MITE, OVICIDAL TEST

N-Methyl-2,4-difluoro-2',4'-dinitro-6'-(trifluoromethyl)diphenylamine (2EC as described in Example 62) was foliar applied under laboratory conditions to detached soybean leaves at rates of 1 to 3 lb/100 gallons (1200 to 3600 ppm) using a $CO_2$ backpack sprayer fitted with a single nozzle boom. Comite 6.75EC and Fundal 4EC at 3.4 and 2 lb/100 gallons (respectively) were included as reference miticides. A single application was made to the lower surface of trifoliate leaves infested with two-spotted spider mite (*Tetranychus urticae*). Prior to application all living mites were brushed off the leaf surfaces leaving only mite eggs for ovicidal evaluation. Following treatment the soybean leaves were incubated in petri dish moist chambers held at room temperature. Four days following treatment microscopic observations were made on the leaves and ratings made on the percent egg hatch as a measure of ovicidal activity.

Four days following treatment the test compound 2EC at rates of 1, 1.5, 2 and 3 lb/100 gallons gave 5.2, 0.5, 0.2 and 0 percent egg hatch (respectively) compared to 94.2 percent hatch in the untreated controls. Fundal also gave 0 egg hatch and Comite resulted in a 16.3 percent hatch.

EXAMPLE 73: TWO SPOTTED SPIDER MITE, FIELD TEST ON PEACH

N-Methyl-2,4-difluoro-2',4'-dinitro-6'-(trifluoromethyl)diphenylamine (2EC as described in Example 62) was foliar applied at rates of 0.25 to 4 lb/100 gallons of spray solution to individual branches of redhaven peach trees infested with two-spotted spider mites (*Tetranychus urticae*). Kelthane 4EC at the rate of 3 lb/100 gallons was included as the reference miticide. Three single-branch replicates were included for each treatment. A single application was made using a $CO_2$ backpack sprayer fitted with a hand-held single nozzle boom. All treatments were made on upper and lower leaf surfaces applying spray solution to the point of runoff. Two days following application, mite counts were made on three leaves picked at random from each single branch treatment. Each leaf was placed under a dissecting microscope and the total number of living mites observed in a 0.5" field adjacent to the midrib was recorded.

Two days after application, the test compound 2EC at 0.25 to 3 lb/100 gallons of spray solution gave 79 to 100 percent mite control with little or no phytotoxicity on peach foliage. Kelthane 4EC at 3 lb/100 gallons gave 98 percent mite control with slight foliar injury. Observations made five days after application revealed that the test compound at 2 to 4 lb/100 gallons was providing 95 to 100 percent mite control. Kelthane was giving perfect mite control at this observation.

EXAMPLE 74: TWO SPOTTED SPIDER MITE, FIELD TEST ON SOYBEANS

N-Methyl-2,4-difluoro-2',4'-dinitro-6'-(trifluoromethyl)diphenylamine (2EC as described in Example 62) was foliar applied to soybeans at rates of 0.125 to 1.5 lb/acre (0.25 to 3 lbs/100 gallons) in a spray volume of 50 gallons per acre. 2,4-Difluoro-2',4'-dinitro-6'-(trifluoromethyl)diphenylamine, as a 2EC of the following composition:

| component | percent |
|---|---|
| 2,4-difluoro-2',4'-dinitro-6'-(trifluoromethyl)diphenylamine | 24.5 |
| Toximul D | 5.0 |
| Toximul H | 5.0 |
| Methyl Cellosolve | 10.0 |
| AN 2L (a solvent mixture of heavy aromatic naphthas and xylenes) | 55.5 | was also evaluated at 0.25 to 1.0 lb./acre. Fundal 4EC at 1 lb/100 gallons and Comite 6.75EC at 1.7 lb/100 gallons were included as reference miticides. A Hagie high-clearance sprayer utilizing compressed air as the propellant and feeding a six-nozzle boom was used in all applications. Treatments were applied twice at seven-day intervals. Each plot consisted of two rows of soybeans 20 feet long, with each treatment replicated four times. Pretreatment evaluations indicated two-spotted spider mite (*Tetranychus urticae*) populations ranging from 0 to 15 mites per 0.5" field under a dissecting microscope. Beet armyworm larvae (*Spodoptera exigua*) were also present on foliage at the time of first application. Observations were made for mites and beet armyworms two and six days following the first and second application.

The N-methyl-2,4-difluoro-2',4'-dinitrol-6'-(trifluoromethyl)diphenylamine applied at 0.125 to 1.5 lb/acre gave no control to marginally acceptable control (0 to 80 percent) of two-spotted spider mite during the course of this experiment, but resulted in only slight foliar injury. The 2,4-difluoro-2',4'-dinitro-6'-(trifluoromethyl)diphenylamine applied at 0.25 to 1 lb./acre gave marginally acceptable to very good (66 to 97 percent) mite control; however, treatments with this compound resulted in slight to moderate foliar phytotoxicity increasing to severe injury in the 1.5 lb./acre treatment following the second application. Fundal treatments failed to give acceptable mite control and caused slight to moderate foliar phytotoxicity. Comite gave acceptable control of mites with little or no plant damage. None of the treatments provided consistently effective control of beet armyworm during the course of this experiment; however, Fundal showed the highest degree of activity against this insect species.

EXAMPLE 75: TWO SPOTTED SPIDER MITE, OVICIDAL TEST

N-Methyl-2,4-difluoro-2',4'-dinitro-6'-(trifluoromethyl)diphenylamine (2EC as described in Example 62) was foliar applied under laboratory conditions to detached soybean leaves at rates of 0.25 and 0.5 lb/100 gallons of spray solution (300 and 600 ppm) compared to Fundal 4EC at 0.125 to 2 lb/100 gallons for determination of ovicidal efficacy against the two-spotted spider mite (*Tetranychus urticae*). Six single trifoliate leaves were treated for each treatment using a $CO_2$ backpack sprayer fitted with a single-nozzle boom. A single application was made to the lower surface of each mite-infested leaf. Prior to application all living mites were brushed off the leaf surfaces leaving only mite eggs for ovicidal evaluation. Following treatment the soybean leaves were incubated in petri dish moist chambers held at room temperature. Six days following treatment microscope observations were made on the leaves and ratings made on the percent egg hatch as a measure of ovicidal activity.

Six days following foliar treatment on detached soybean leaves, the test compound at 0.25 and 0.5 lb/100 gallons and Fundal 4EC at 0.125 to 2 lb/100 gallons resulted in significantly less hatch of two-spotted spider mite eggs than the untreated controls. Under the conditions of this laboratory experiment, the test compound at rates of 0.25 to 0.5 lb/100 gallons provided fair to excellent ovicidal activity against the two-spotted spider mite on detached soybean leaves.

EXAMPLE 76: TWO SPOTTED SPIDER MITE, FIELD TEST ON SOYBEANS

N-Methyl-2,4-difluoro-2',4'-dinitro-6'-(trifluoromethyl)diphenylamine (2EC as described in Example 62) was foliar applied to soybeans at rates of 0.25 to 4 lb/100 gallons of solution and the same compound as a 50WO (Example 55) was evaluated at 1 to 4 lb/100 gallons. Comite 6.75EC at 3.4 lb/100, Kelthane 4EC at 3 lb/100, and Fundal 4EC at 3 lb/100 gallons of solution were included as reference miticides. Applications were made using a $CO_2$ backpack sprayer fitted with a single-nozzle boom covering all leaf surfaces to the point of runoff. One application was made on the soybeans with four, single-plant replicates per treatment. Mite counts were made on three leaves from each plant recording the total number of living mites observed in a 0.5" microscope field adjacent to the midrib. Two-spotted spider mites (*Tetranychus urticae*) were present at a population of 50 to 150 mites per entire leaflet at the time of application. In addition to living mite counts, observations were made on leaves which had been removed from treated plants brushed free of adult and nymphal mites to determine ovicidal activity of the compounds. Detached leaves were incubated for three days prior to ovicidal evaluations.

In both formulations, the test compound applied to soybeans at rates of 1 to 4 lb/100 gallons gave 94 to 99 percent control of two-spotted spider mite two days after application. The 2EC formulation gave slight phytotoxicity at these rates; however, the 50WP formulation showed slight injury only at the 4 lb/100 gallon rate. Observations made five days after application showed both formulations of test compound at 2 and 4 lb/100 gallons continuing to provide 91 to 97 percent mite control. Both formulations of test compound at 1 to 4 lb/100 gallons showed 82 to 100 percent reduction in egg hatch (ovicidal activity). Fundal also gave 100 percent ovicidal activity; however, neither Comite or Kelthane performed well as ovicides. Nymph and adult forms of the predatory mite (*Typhlodromus occidentalis*) were frequently observed on leaves treated with the test compounds however, individuals of this beneficial species were seen less often in the Comite, Kelthane and Fundal treatments.

EXAMPLE 77: TWO SPOTTED SPIDER MITE, FIELD TEST ON MARIGOLDS

N-Methyl-2,4-difluoro-2',4'-dinitro-6'-(trifluoromethyl)diphenylamine (2EC as described in Example 62) was evaluated for the control of two-spotted spider mite (*Tetranychus urticae*). Marigolds, variety King Tut, were grown in 4 inch round pots until they were 6 to 8 inches tall and then were infested with two-spotted spider mite. Mites were allowed to become established on the potted plants, then the test compound and the references Kelthane 10.3% EC (Dicofol) and Vendex 50W (Fenbutatin-oxide) were foliar applied at 10, 100, 1000 ppm and sprayed to runoff. Each treatment was replicated four times.

Evaluations were made 24 hours, 4 days and 8 days following treatment by counting the number of adult mites and mite nymphs per five leaves per pot. The test compound provided excellent control of two-spotted spider mite; this control was comparable to the references Kelthane and Vendex at comparable rates. In addition, the observation was made that the test compound appeared to have ovicidal activity against two-spotted spider mite eggs.

EXAMPLE 78: TWO SPOTTED SPIDER MITE, FIELD TEST ON EGGPLANT

N-Methyl-2,4-difluoro-2',4'-dinitro-6'-(trifluoromethyl)diphenylamine 2EC (Example 62) was foliar applied at rates of 0.5, 1, 2 and 2.5 lb/acre to a young eggplant (*Solanum melongena* var. *esculentum*) crop having a moderate infestation of two-spotted spider mites (*Tetranychus urticae*). Comite 6.75EC at 1.25 lb/acre was applied as a commercial reference. The first three applications were made at weekly intervals with a small plot spray machine using a $CO_2$ spray system equipped with a three nozzle boom applying a spray volume of 100 gallons per acre. The last two treatment applications were made at two week intervals using the same equipment but with a total of five spray nozzles to achieve full coverage of the rapidly growing plants. Three plants in each of the twenty foot treatment plots were flagged and live adult mites on the entire plant or a given number of leaves were counted both pretreatment and at various evaluation dates.

Seven days after the first treatment application, the test compound was providing 74 percent control of two-spotted spider mites at the low rate but 89 to 97 percent control at the 1 to 2.5 lb/acre rates. Comite 6.75EC at 1.25 lb/acre provided 94 percent control at this first observation. Spider mite populations in the control plots increased dramatically during this experiment. Evaluations five days after the second application indicated that the test compound provided 96 percent control at 1 lb/acre and 98 percent control at 2 and 2.5 lb/acre. After the second application, the eggplant foliage was moderately infested with tomato pinworm (*Keiferia lycopersicella*). The test compound provided fair protection from pinworm damage as compared to the control plots or the Comite treatment.

Six days after the third application the test compound provided fair (76 to 79%) spider mite control at the 0.5 lb/acre rate. At 1 to 2.5 lb/acre, the test compound provided 96 to 99 percent control with Comite giving 96 percent control. A week later or 13 days after this third application, mite control had declined to 85 percent at 1 lb/acre and 96 percent with the 2 and 2.5 lb/acre rates. Comite control was at 90 percent 13 days after the third application. A fourth application was made two weeks after the third application and the test compound provided 73 to 83 percent control at all rates. A fifth treatment was applied to the large, fruit setting eggplant crop. Additional mite counts were not made but crop injury ratings were made at crop maturity, 37 days after the last application and a total of 77 days from the first treatment date.

The test compound did not cause injury to the eggplant test crop. Late season crop vigor ratings indicated little difference between the test compound and Comite with all treatments being 12 to 25 percent more vigorous than the controls. The eggplant crop was harvest twice with all fruit removed at the last harvest. Total fruit weight, number of fruit, weight of fruit per plant and individual fruit weight seemed to indicate that the test compound and Comite were equal to or better than the controls.

EXAMPLE 79: CITRUS RUST MITE, FIELD TEST ON TEMPLE ORANGE

N-Methyl-2,4-difluoro-2',4'-dinitro-6'-(trifluoromethyl)diphenylamine (2EC as described in Example 62) was applied as multiple treatments at rates of 0.5, 1, 1.5 and 2 lb/acre to young bearing (two year old), four to five foot Temple orange (*Citrus sinensis*) trees heavily infested with citrus rust mites (*Phyllocoptruta oleivora*). Comite 6.75EC at 1.25 lb/acre and Dimilin 25W at 1 lb/acre were applied as reference treatments. Applications were made using a $CO_2$ backpack sprayer unit with a single nozzle hand-held boom to achieve a full coverage foliar spray at the commercially recommended volume of 1000 gallons per acre. A total of 1390 mls. was applied to each of two trees considered to occupy a 4×4 foot spray area. One-half of each tree was designated as one of four experimental replications.

Ten leaves per replication (20 per tree), which had a population in excess of 50 to 100 citrus rust mites, were tagged prior to treatment. These pretagged leaves were used in subsequent mite control evaluations when several leaves were collected for viewing under a microscope for counts of live citrus rust mites in four (two upper surface and two lower surface) 8 mm. diameter area on each leaf.

A second treatment application was made four days following the first application in an attempt to obtain control of immature mites which hatched after the initial treatment. Rainfall in the amount of 1.06 inches occurred approximately six hours after this second application. A third application was made three weeks after the first application. A light rain fell within 20 minutes of this third application with a total of 0.9 inch occurring within 24 hours.

Evaluations one and four days after the first application indicated the test compound at 2 lb/acre provided 81 and 68 percent control, respectively. The 1 and 1.5 lb/acre rates provided only 47 and 41 percent control, respectively, at one day, and 42 and 41 percent control, respectively, at four days. Comite was 85 and 75 percent at these two early evaluations while Dimilin activity increased from 28 to 50 percent control. Three days after the second application citrus rust mite control had increased to 75, 69 and 82 percent with the test compound at 1, 1.5 and 2 lb/acre, respectively. Comite provided 92 percent control and control with Dimilin had increased to 79 percent. At 15 days after the second application, mite control with the test compound was unsatisfactory while Comite and Dimilin provided 92 and 93 percent control. Rainfall within six hours after the second application probably influenced the duration of control of the test compound. A third application was made 16 days after the second application; however, light rain also occurred after this third application. Twelve days after the third application and after a total of 4.26 inches of rainfall during that time, activity with the test compound had increased at some rates and decreased at others, and was generally variable and unsatisfactory. Control with Comite had also decreased to 79 percent while control with Dimilin had increased to 98 percent.

None of the multiple application treatments in this experiment caused injury to the foliage or fruit of these young Temple orange trees.

EXAMPLE 80: CITRUS RED MITE, FIELD TEST ON VALENCIA ORANGE

N-Methyl-2,4-difluoro-2',4'-dinitro-6'-(trifluoromethyl)diphenylamine (2EC as described in Example 62) was foliar applied to selected branches of orange trees, variety Valencia, for control of the citrus red mite (*Panonychus citri*). Morestan 25WP (oxythioquinox) and Kelthane 1.6 EC (dicofol) were employed as reference standards. The selected branches were sprayed with a single nozzle boom until all of the leaf surfaces were wet, with spray unitage expressed as pounds of active chemical per 100 gallons of spray solution and 1 lb./100 gallons providing a concentration of 1200 ppm. Two treated leaves per plot were placed in petri dish moist chambers after removing nymphs and adult mites with a camel hair brush from the leaf surfaces. Leaves were kept under constant 78 degrees temp. and 24 hr. light in the greenhouse. Live nymph and adult mites were counted on 10 orange leaves taken at random from each plot. The entire leaf surface (upper and lower) was scanned under a dissecting microscope and the number of living mites was recorded. Total number of adult live mites were visually counted from 10 orange leaves taken at random from each treatment in the field.

The results were as set forth in the following table.

TABLE VI

| CITRUS RED MITE FIELD TEST | | |
|---|---|---|
| | | % control of Citrus Red Mite |
| Compound | Concentration lbs./100 gal. | 2 days post treatment | 6 days post treatment |
| N—methyl-2,4-difluoro-2',4'-dinitro-6'-(trifluoromethyl)-diphenylamine | 1 | 35.1 | 61.1 |
| | 2 | 73.0 | 78.1 |
| | 4 | 83.8 | 79.8 |
| Morestan | 1 | 67.6 | 97.2 |
| Kelthane | 3.2 | 75.7 | 86.9 |

No crop injury was noted in any of the treatments.

EXAMPLE 81: TWO SPOTTED SPIDER MITE, FIELD TESTS ON SOYBEANS

Several of the compounds to be employed in accordance with the present invention were evaluated for the control of two-spotted spider mite (*Tetranychus urticae*) on plots of 2-month-old soybeans with a moderate to heavy pretreatment population of mites. Each was employed as an emulsifiable concentrate formulated in general as described in Example 62. Kelthane 1.6 EC was employed as a reference control. Each compound was applied in a spray.

The results were as set forth in the following table.

TABLE VII
TWO SPOTTED SPIDER MITE FIELD TEST

| Compound | lb. per acre | % Control of two-spotted spider mite | | % crop injury | |
|---|---|---|---|---|---|
| | | 2 days post-treatment | 6 days post-treatment | 5 days post-treatment | 9 days post-treatment |
| N—Methyl-4-fluoro-2',4'-dinitro-6'-(trifluoromethyl)-diphenylamine | 0.5 | 70.2 | 90.9 | 0 | 2.5 |
| | 1 | 93.5 | 84.4 | 5 | 17.5 |
| | 2 | 77.5 | 86.2 | 15 | 37.5 |
| N—Methyl-3-(trifluoromethyl)-2',4'-dinitro-6'-(trifluoromethyl)-diphenylamine | 0.5 | 93.8 | 88.5 | 0 | 0 |
| | 1.0 | 97.1 | 89.7 | 2.5 | 17.5 |
| | 2.0 | 97.7 | 98.2 | 25.0 | 37.5 |
| N—Methyl-2,4-difluoro-2',4'-dinitro-6'-(trifluoromethyl)-diphenylamine | 0.5 | 91.0 | 92.1 | 0 | 0 |
| | 1.0 | 96.9 | 90.3 | 0 | 0 |
| | 2.0 | 97.7 | 96.8 | 0 | 0 |
| N—Methyl-4-bromo-2',4'-dinitro-6'-(trifluoromethyl)-diphenylamine | 0.5 | 75.4 | 93.8 | 0 | 15.0 |
| | 1.0 | 90.8 | 80.9 | 22.5 | 35.0 |
| | 2.0 | 97.7 | 98.5 | 35.0 | 55.0 |
| N—Methyl-4-chloro-2',4'-dinitro-6'-(trifluoromethyl)-diphenylamine | 0.5 | 90.2 | 59.8 | 0 | 0 |
| | 1.0 | 95.2 | 79.1 | 0 | 0 |
| | 2.0 | 96.7 | 90.0 | 0 | 2.5 |
| Kelthane | 0.5 | 70.0 | 70.6 | 0 | 0 |

EXAMPLE 82: APPLE RUST MITE

Each of N-methyl-2,4-difluoro-2',4'-dinitro-6'-(trifluoromethyl)diphenylamine and N-methyl-3-(trifluoromethyl)-2',4'-dinitro-6'-(trifluoromethyl)-diphenylamine was evaluated for the control of natural infestations of apple rust mite (*Aculus schlechtendali*) on detached apple branches. Infection was determined by examination of a leaf from each branch being used in the test. The cut ends of the branches were placed in water during the test.

Each compound was formulated by dissolving 110 mg. in 2 ml. of a solvent (1:1 acetone:ethanol containing per liter 23 grams of Toximul R and 13 grams of Toximul S) and thereafter adding 108 ml. of water. This provided a first treating formulation comprising 1000 ppm of test compound. Serial dilutions of a portion of this formulation provided treating formulations of lower compound concentration. A solvent control was also employed.

Twigs were sprayed to the point of run-off and rated 24 hours later. Ratings were made by counting the number of mobile mites on the first fully expanded leaf of each branch and on the first hardened leaf of each branch. Counting ceased at 200 mites/leaf. the ratings were then converted into percent control:

$$\% \text{ Control} = \frac{\text{No. of survivors in control} - \text{no. of survivors in treated}}{\text{No. of survivors in control}} \times 100$$

Results were as set forth in the following table.

TABLE VIII
APPLE RUST MITE

| Compound | Conc. (ppm.) | Percent Control of Apple Rust Mite |
|---|---|---|
| N—methyl-2,4-difluoro-2',4'-dinitro-6'-(trifluoromethyl)-diphenylamine | 1000 | 100 |
| | 100 | 44 |
| | 50 | 0 |
| N—methyl-3-(trifluoromethyl)-2',4'-dinitro-6'-(trifluoromethyl)diphenylamine | 1000 | 100 |
| | 100 | 100 |
| | 50 | 99 |

EXAMPLE 83: EUROPEAN RED MITE, FIELD TEST

Each of N-methyl-2,4-difluoro-2',4'-dinitro-6'-(trifluoromethyl)diphenylamine and N-methyl-3-(trifluoromethyl)-2',4'-dinitro-6'-(trifluoromethyl)-diphenylamine was evaluated for the control of natural infestations of European red mite (*Panonychus ulmi*) on red delicious apple trees.

Each compound was formulated as a 1.5 lbs./gallon emulsifiable concentrate (see Example 62), then diluted with water and sprayed onto the infested trees at the rate of 200 gallons per acre (1.8 gallons per tree). There were two trees per treatment, except that six trees were used for the water-only control. A second application was made eight days later.

Evaluations of mite control were made periodically beginning 1 day after the first treatment and continuing until 29 days after the second treatment. Each evaluation was made as follows. Five tight leaf clusters were selected from each tree, one from each quadrant and one from the center of the tree. Mite counts were made using a mite brushing machine and a 20X dissecting microscope. Results were as reported in the following table.

TABLE IX
EUROPEAN RED MITE, FIELD TEST ON RED DELICIOUS APPLE TREES

| Compound | Appln. Rate (lbs./acre) | Percent Control | | | | | | | |
|---|---|---|---|---|---|---|---|---|---|
| | | Subsequent to first treatment | | | Subsequent to second treatment | | | | |
| | | 1 day | 4 days | 7 days | 1 day | 4 days | 12 days | 15 days | 29 days |
| N—methyl-2,4-difluoro-2',4'-dinitro-6'-(trifluoromethyl)diphenylamine | 2 | 95 | 93 | 10.5 | 96 | 92 | 94 | 87 | 90 |
| | 1 | 95 | 80 | 0 | 84 | 84 | 87 | 67 | 83 |
| | 0.5 | 79 | 46 | 0 | 53 | 81 | 50 | 38 | 47 |
| | 0.25 | 58 | 52 | 0 | 54 | 39 | 33 | 22 | 0 |
| N—methyl-3-(trifluoromethyl)-2',4'-dinitro-6'-(trifluoromethyl)diphenylamine | 2 | 95 | 66 | 17 | 69 | 51 | 87 | 69 | 44 |
| | 1 | 84 | 57 | 38 | 58 | 48 | 52 | 43 | 47 |
| | 0.5 | 74 | 52 | 0 | 43 | 22 | 16 | 0 | 0 |
| | 0.25 | 43 | 22 | 0 | 9 | 0 | 0 | 0 | 0 |
| Omite (reference) | 3 | 90 | 90 | 79 | 87 | 92 | 97 | 90 | 90 |
| Control (Mean number of mites) | — | 76.66 | 117.33 | 193.33 | 229.33 | 248.66 | 296.66 | 240.66 | 435.33 |

EXAMPLE 84: TWO SPOTTED SPIDER MITE, EVALUATION OF POTENTIAL FOR RESISTANCE

N-Methyl-2,4-difluoro-2',4'-dinitro-6'-(trifluoromethyl)diphenylamine was evaluated to determine whether mites would develop resistance to the compound. The compound was formulated as described in Example 82, and diluted to a concentration of 50 ppm, the concentration believed to be the $LD_{95}$.

Bean plants (variety Bountiful Bush) were grown to the true leaf stage and infested with two spotted spider mite (*Tetranychus urticae*). Forty-eight hours later the plants were treated, and forty-eight hours after treatment, the plants were evaluated for percent control. The survivors from the treated plants were allowed to develop until of a sufficient number to infest a new group of bean plants.

The foregoing procedures were repeated for a total of 10 treatments. The results were as reported in the following table.

TABLE X
TWO SPOTTED SPIDER MITE, MULTIPLE APPLICATIONS

| Population | Percent Control |
|---|---|
| 1st | 93 |
| 2nd | 95 |
| 3rd | 97 |
| 4th | 95.5 |
| 5th | 94 |
| 6th | 97 |
| 7th | 97 |
| 8th | 94 |
| 9th | 95 |
| 10th | 94 |

EXAMPLE 85: COMPARATIVE PHYTOTOXICITY TESTS

As noted above, the compounds to be employed in accordance with the present invention exhibit little or no phytotoxicity at use rates. This absence of phytotoxicity is surprising in view of the significant phytotoxicity of many diphenylamines of the prior art. These differences are illustrated by the following greenhouse evaluation for crop response of soybeans to various diphenylamines.

Each compound was formulated in a small amount of 50:50 ethanol:acetone and Tween 20, then diluted with water and separated into multiple formulations containing the respective compound at various concentrations. Because of preliminary indications of higher phytotoxicity of an N-H diphenylamine in comparison with its corresponding N-CH3 diphenylamine (see Example 67 hereinabove), different concentrations were necessarily evaluated in an attempt to determine the highest concentration of the spray formulation free of phytotoxicity. Generally, N-H compounds were evaluated at 125, 62.5 and 31.25 ppm, and N-CH3 compounds, at 4000, 2000 and 1000 ppm. Where necessary, selected compounds were retested at lower concentrations. Treated plants were held and observed for leaf distortion and leaf necrosis. However, any other kind of apparent response was noted. Each formulation was sprayed onto Kent-variety soybeans which were 21-days old (two fully-expended trifoliate leaves and a juvenile are present). There were two replicates per treatment, and each replicate consisted of two plants. Not all of the treatments were conducted at the same time, but each group of treatments included a solvent control and an untreated control. Neither the solvent check nor the untreated check exhibited any phytotoxicity in any of the tests.

The results of this evaluation for phytotoxicity were as set forth in the following table. Blanks in the table indicate that the compound in question was not tested. All data on a single line represents tests conducted at the same time.

TABLE XI
COMPARATIVE PHYTOTOXICITY TEST

| 2',4'-Dinitro-6'-(trifluoromethyl)-diphenylamine compound-substitution on ring | Highest concentration (ppm) free of phytotoxicity | | | |
|---|---|---|---|---|
| | N—H | N—CH$_3$ | N—C$_2$H$_5$ | N—n-C$_3$H$_7$ |
| 2-F | 62.5 | 4000 | | |
| 3-F | 31.25 | 4000[1] | | |
| 3-F | 31.25 | 500 | | |
| 4-F | 31.25 | 2000 | | |
| 2,4-di F | 31.25 | 1000 | | |
| 2,4-di F | <31.25 | | 4000 | |
| 2,4-di F | 15.62 | 4000 | | |
| 2,5-di F | <31.25 | 2000 | | |
| 2,6-di F | 31.25 | 4000 | | |
| 3,4-di F | <31.25 | 1000 | | |
| 2,4,6-tri F | <31.25 | 4000 | | |
| 2,3,5,6-tetra F | <31.25 | 4000 | | |
| 2,3,4,5,6-penta F | <31.25 | 4000 | | |
| 2-Cl | <31.25 | 4000 | | |
| 3-Cl | <31.25 | 4000 | | |
| 4-Cl | <31.25 | 4000 | | |
| 3,5-di Cl | <31.25 | 4000 | | |
| 2,4,6-tri Cl | <31.25 | 1000 | | |
| 2,4,6-tri Cl | <31.25 | | 1000 | 1000 |
| 2,3,4,5,6-penta Cl | 62.5 | 4000 | | |
| 3-Br | <31.25 | 4000 | | |
| 4-Br | <31.25 | 4000 | | |
| 2,4-di Br | <31.25 | 4000 | | |
| 4-I | <31.25 | 4000 | | |
| 3-CF$_3$ | 7.81 | 4000 | | |
| 4-CF$_3$ | <31.25 | <1000 | | |
| 4-CF$_3$ | <7.81 | 1000 | | |
| 2-Cl—5-CF$_3$ | <31.25 | <1000 | | |
| 2-Cl—5-CF$_3$ | 7.81 | 250 | | |

[1] Neither leaf distortion nor leaf necrosis was noted at any of the three rates tested; however, leaf chlorosis was noted and was rated 4 at 1000 ppm, 6 at 2000 ppm, and 6 at 4000 ppm (on a scale of 0–10 with 0 = no effect and 10 = severe effect).

The compounds to be employed in the above described insecticidal and arachnicidal uses also exhibit ectoparasiticidal activity when applied to the locus of ectoparasites on the surface of warm blooded animals. The compounds control ectoparasites by contact action.

Parasitic insect and acarina are legion and include species which are bloodsucking as well as flesh eating, and species which are parasitic during all of their life cycle or only part of their life cycle, such as only the larval or only the adult stage. Representative species include the following:

| Parasites of Horses | |
|---|---|
| horsefly | Tabanus spp. |
| stable fly | Stomoxys calcitrans |
| black fly | Simulium spp. |
| horse sucking louse | Haematopinus asini |
| mange mite | Sarcoptes scabiei |
| scab mite | Psoroptes equi |
| Parasites of Bovines | |
| horn fly | Haematobia irritans |
| cattle biting louse | Bovicola bovis |
| short-nosed cattle louse | Haematopinus eurysternus |
| long-nosed cattle louse | Linognathus vituli |
| tsetse fly | Glossina spp. |

| | |
|---|---|
| stable fly | *Stomoxys calcitrans* |
| horse fly | *Tabanus* spp. |
| cattle follicle mite | *Demodex bovis* |
| scab mite | *Psoroptes ovis* |
| cattle tick | *Boophilus microplus* and *decoloratus* |
| Gulf Coast tick | *Amblyomma maculatum* |
| Lone-Star tick | *Amblyomma americanum* |
| ear tick | *Otobius megnini* |
| Rocky Mountain spotted fever tick | *Dermacentor andersoni* |
| blowfly larva | *Callitroga hominivorax* |
| assassin bug | *Reduvius* spp. |
| mosquito | *Culiseta inornata* |
| brown ear tick | *Rhipicephalus appendiculatus* |
| red-legged tick | *Rhipicephalus evertsi* |
| bont tick | *Amblyomma* sp. |
| bont legged tick | *Hyalomma* sp. |
| Parasites of Swine | |
| hog louse | *Haematopinus suis* |
| chigoe flea | *Dermatophilus penetrans* |
| Parasites of Sheep and Goats | |
| bloodsucking body louse | *Haematopinus ovillus* |
| bloodsucking foot louse | *Linognathus pedalis* |
| sheep ked | *Melophagus ovinus* |
| scab mite | *Psoroptes ovis* |
| greenbottle fly | *Lucilia sericata* |
| black blowfly | *Phormia regina* |
| secondary screw-worm | *Callitroga macellaria* |
| sheep blowfly | *Lucilia cuprina* |
| Parasites of Poultry | |
| bed bug | *Cimex lectularius* |
| Southern chicken flea | *Echidnophaga gallinacea* |
| fowl tick | *Argas persicus* |
| chicken mite | *Dermanyssus gallinae* |
| scaly-leg mite | *Knemidokoptes mutans* |
| deplumbing mite | *Knemidokoptes gallinae* |
| Parasites of Dogs | |
| horse fly | *Tabanus* spp. |
| stable fly | *Stomoxys calcitrans* |
| mange mite | *Sarcoptes scabiei* |
| dog follicle mite | *Demodex canis* |
| dog flea | *Ctenocephalis canis* |
| American dog tick | *Dermacentor variabilis* |
| brown dog tick | *Rhipicephalus sanguineus* |

Although the parasites are listed above as associated with a particular host, in fact the various parasites freely attack other animals as well.

The rate, timing, and manner of effective application will vary widely with the identity of the host animal, the identity of the parasite, the degree or parasiticidal attack, and other factors. The compounds can be applied to the surface of host animals by spraying, dipping, spot application or drenching, utilizing a liquid formulation containing the compound. The compounds can also be applied in dusts which can be applied to the surface of animals or supplied to the animals in dust bags or as "back rubbers" for optional use by the animals. Application can be made periodically over the entire lifespan of the host, or for only a peak season of parasitic attack. In general, ectoparasite control is obtained with liquid formulations containing from about 0.00005 to 5.0 percent of compound, and preferably from about 0.00005 to about 1.0 percent of compound.

For application to host animals, the present compounds are formulated in conventional manners, with one or more physiologically acceptable adjuvants, which can be any substance that aids in the implementation of the ectoparasiticidal activity of the compounds of the present invention. The adjuvant can be a solvent, an inert diluent, a surface active agent, a suspending agent, and the like.

The ectoparasiticidal activity of the compounds of the present invention is illustrated by the following examples.

EXAMPLE 86: BLOWFLY LARVAE AND ADULT HOUSEFLY, BOVINE SERUM TEST

Representative compounds to be employed in accordance with the present invention were evaluated against larvae of blowfly (*Phormia regina*) and against adult housefly (*Musca domestica*).

The test was conducted as follows: 1 ml. of DMF was added to 1 mg. of compound in a 15 ml. test tube. Distilled water (9 ml.) was added. A 0.2 ml. portion of this stock solution was placed in a 6.5 ml. test tube and 1.8 ml. of bovine serum was added, yielding a 10 pp. test solution. To obtain a 20 ppm test solution, the amount of test compound was increased accordingly. A dental wick was placed in the test tube and approximately 40 to 50 blowfly larvae were placed on the wick. The test tube was covered with a cotton ball and incubated at 27° C. for 24 hours, at which time larval mortality counts were made. Efficacy was calculated as follows:

$$\frac{\text{total larval population} - \text{no. live larvae}}{\text{total larval population}} \times 100$$

(larval population was adjusted for normal mortality in the control). Ratings were made according to the following scale 0 = none dead
1 = <50% dead
2 = 51–75% dead
3 = 76–90% dead
4 = 91–99% dead
5 = 100% dead The test against adult housefly was conducted in the same procedure except that the saturated wick was placed in a petri dish and approximately 25 chilled houseflies were placed in the dish. The dish was covered and incubated at 27° C. and 70% relative humidity.

The results of these tests are set forth in the following table.

TABLE XII
BLOWFLY LARVAE AND ADULT HOUSEFLY, BOVINE SERUM TEST

| Compound of Example No. | Concentration of Compound in ppm. | Rating Blowfly Larvae | Rating Adult Housefly |
|---|---|---|---|
| 2  | 10 | 0 | — |
| 2  | 20 | 0 | — |
| 3  | 10 | 5 | — |
| 3  | 10 | 2 | — |
| 3  | 10 | — | 5 |
| 3  | 10 | — | 3 |
| 4  | 10 | 5 | — |
| 4  | 10 | 5 | — |
| 4  | 20 | — | 3 |
| 4  | 20 | — | 5 |
| 5  | 10 | 5 | — |
| 5  | 20 | — | 3 |
| 10 | 10 | 0 | — |
| 10 | 10 | 0 | — |
| 10 | 10 | — | 1 |
| 11 | 10 | 5 | — |
| 11 | 10 | — | 5 |
| 14 | 10 | 0 | — |
| 14 | 20 | 0 | — |
| 15 | 10 | 5 | — |
| 15 | 10 | 0 | — |
| 15 | 10 | 5 | — |
| 15 | 10 | 0 | — |
| 15 | 10 | — | 5 |

TABLE XII-continued
BLOWFLY LARVAE AND ADULT HOUSEFLY, BOVINE SERUM TEST

| Compound of Example No. | Concentration of Compound in ppm. | Rating Blowfly Larvae | Rating Adult Housefly |
|---|---|---|---|
| 15 | 10 | — | 4 |
| 16 | 10 | 5 | — |
| 16 | 10 | 5 | — |
| 16 | 10 | — | 5 |
| 16 | 20 | — | 5 |
| 18 | 10 | 0 | — |
| 18 | 10 | 0 | — |
| 18 | 20 | 0 | — |
| 20 | 20 | 3 | — |
| 20 | 20 | — | 1 |
| 23 | 10 | 5 | — |
| 23 | 10 | 5 | — |
| 23 | 10 | — | 4 |
| 23 | 10 | — | 5 |
| 24 | 10 | 5 | — |
| 24 | 10 | — | 5 |
| 25 | 10 | 5 | — |
| 25 | 10 | — | 4 |
| 26 | 10 | 0 | — |
| 26 | 10 | 0 | — |
| 26 | 10 | — | 4 |
| 28 | 10 | 5 | — |
| 28 | 10 | — | 5 |
| 30 | 10 | 5 | — |
| 30 | 10 | — | 5 |
| 31 | 10 | 1 | — |
| 31 | 10 | 5 | — |
| 31 | 10 | — | 5 |
| 33 | 10 | 0 | — |
| 33 | 10 | 0 | — |
| 34 | 10 | 0 | — |
| 34 | 10 | 0 | — |
| 34 | 10 | 5 | — |
| 34 | 10 | — | 3 |
| 34 | 10 | — | 4 |
| 34 | 10 | — | 2 |
| 35 | 10 | 4 | — |
| 35 | 10 | 5 | — |
| 35 | 10 | — | 1 |
| 35 | 10 | — | 1 |
| 37 | 10 | 5 | — |
| 37 | 10 | 5 | — |
| 37 | 10 | 5 | — |
| 37 | 10 | — | 5 |
| 37 | 10 | — | 1 |
| 37 | 10 | — | 4 |
| 38 | 10 | 5 | — |
| 38 | 10 | — | 4 |
| 39 | 10 | 5 | — |
| 39 | 10 | 5 | — |
| 39 | 10 | — | 4 |
| 39 | 10 | — | 1 |
| 40 | 10 | 0 | — |
| 41 | 10 | 5 | — |
| 41 | 20 | — | 2 |
| 44 | 10 | 5 | — |
| 44 | 10 | 5 | — |
| 44 | 10 | 5 | — |
| 44 | 10 | — | 4 |
| 44 | 10 | — | 5 |
| 44 | 10 | — | 5 |
| 45 | 10 | 5 | — |
| 45 | 20 | — | 1 |
| 47 | 20 | 5 | — |
| 47 | 20 | 0 | — |
| 47 | 20 | — | 1 |
| 48 | 20 | 5 | — |
| 48 | 20 | 5 | — |
| 48 | 20 | — | 1 |
| 48 | 20 | — | 0 |

EXAMPLE 87: PSOROPTES MITES, IN VITRO

Several compounds were evaluated for the control of Psoroptes mite in vitro. In this test procedure, about 20–25 adult or nymphal mites were put in 2.5×2.5-cm "tea-bags" made from heat-sealable rice paper. Three bags containing mites were dipped in each concentration of the test compound for 30 seconds and then allowed to dry at room temperature and ambient humidity. The bags were opened at 24 hour posttreatment, and the mites were observed with the aid of a dissecting microscope and classified as dead or alive. Mites which were immobile or had feeble leg movement were considered dead. Mites able to travel in a normal manner were scored as alive. Mites that served as controls were dipped in dilute solvent and emulsifier at concentrations equivalent to those used in test compound emulsions.

The test compound was initially evaluated at a concentration of 0.1%, then at lower concentrations until the mortality was less than 100%.

N-Methyl-2,4-difluoro-2',4'-dinitro-6'-(trifluoromethyl)diphenylamine gave >90% control of Psoroptes at each of two concentrations, 0.005 and 0.00005%.

N-Methyl-4-bromo-2',4'-dinitro-6'-(trifluoromethyl)diphenylamine gave 100% control at 0.1 percent concentration and <100% control at 0.01 percent concentration.

EXAMPLE 88: STABLE FLY TEST

N-Methyl-4-bromo-2',4'-difluoro-6'-(trifluoromethyl)diphenylamine was evaluated for the control of stable flies (*Stomoxys calcitrans*) in a spot-test on cattle.

In this test, areas on the sides of a bovine were sprayed with a solution of the test compound. Each area was 6 inches in diameter and received 5 ml. of solution. There were five test areas on each side of the animal, positioned so as to minimize cross-contamination. During the test period the animals were confined in individual stanchions. Two sun lamps, one directed toward the treated spots on each side of a test animal, were turned on for a period of 4 hours each day. Each lamp was about 2 meters from the floor and 1 meter from the animal and positioned so that all treated spots received about the same amount of radiation.

Cages, made by soldering screen wire in a mason-jar ring, were used to confine adult stable flies, *Stomoxys calcitrans* (L.), to the treated spots. Twenty-five 3- to 6-day-old female flies that had not fed for about 18 hours were exposed in a cage to a spot for 20 minutes. Then the cage with the flies was removed and placed in the laboratory at 27° C. and 60–70% relative humidity. The number of flies that had fed and the number that had been knocked down were recorded, a square of cotton soaked in blood diet was placed on each cage, and the flies were held for 24 hours when mortality was recorded.

Compounds were tested for both repellency and toxicity at an initial concentration of 5%. Repellency was indicated when less than 20% of the flies had fed during the 20 minute exposure period. Toxicity was indicated when 90% or more of the flies were dead at 24 hours. Pyrethrins at 0.05%, which exhibit repellent activity for 4 days, and methoxychlor at 0.5%, which is effective as a toxicant for 8 days, were used as standards for comparison.

Compounds were rated according to the following classifications:

| | Repellency |
|---|---|
| Class I | Ineffective at 1 day |
| Class II | Effective at 1 day |

| | |
|---|---|
| Class III | Effective for 2–3 days |
| Class IV | Effective for 4 or more days |
| Toxicity | |
| Class I | Ineffective at 1 day |
| Class II | Effective at 1 day |
| Class III | Effective for 4 days |
| Class IV | Effective for 8 or more days |

Compounds that are rated Class IV as a repellent or a toxicant at 5% are routinely tested at lower concentrations until a Class IV rating is no longer obtained.

For a description of the development of the spot-test technique, see Roberts et al., 1960, "Methods for the evaluation of stable fly toxicants and repellents", J. Econ. Entomol. 53(2): 301–3.

N-Methyl-4-bromo-2',4'-difluoro-6'-(trifluoromethyl)diphenylamine was rated as a Class II toxicant and a Class I repellent at 0.5 concentration in the spray solution.

EXAMPLE 89: PSOROPTIC MITES, IN VIVO

Each of N-methyl-2,4-difluoro-2',4'-dinitro-6'-(trifluoromethyl)diphenylamine and N-methyl-3-(trifluoromethyl)-2',4'-dinitro-6'-(trifluoromethyl)-diphenylamine was evaluated for the control of Psoroptic mites, either *Psoroptes cuniculi*, the ear canker mite of rabbits, or *Psoroptes ovis* (Hering), the common scabies mite of cattle. The test was conducted by the method of Fisher et al., 1979, Southwest. Entomol. 4(3):249–253, and Fisher and Wilson, 1981, Insect. Acaric. Test 6:206–207.

In this test method, all rabbits wear plastic collars to restrict grooming and both ears of each rabbit tested are at least one-half filled with canker and scabs. The compound to be tested is formulated as an emulsifiable concentrate in xylene:Triton X-100 (65:10). Solutions containing 1.0% are prepared in 25 ml volumes and administered as ear washes to the rabbits. Each ear is filled with test solution, held, and massaged gently for at least 1 min. The outside of each ear and the area around the head and neck is swabbed. Control rabbits are treated with the appropriate solvent system in the same manner. At weekly intervals the ears of the treated rabbits are checked for live mites with an otoscope. If live mites cannot be seen by 6 weeks (42 days), the ear canals are swabbed and the swabs examined for live mites with the aid of a dissecting microscope. If complete elimination of mites and scabs is obtained at 1.0%, more dilute concentrations are tested until the compound fails to eliminate all the mites. The effectiveness of the various treatments are classified by the following rating system:

A—No reduction in the number of mites or amount of scab.
B—Initial reduction in the number of mites and scabs; mite population recovers soon.
C—Near complete elimination of mites and scabs from ears; mites are not found until end of test.
D—Complete elimination of mites and scabs from ear.

Each of the subject compounds was rated as "D" at each of the two concentrations which were tested, 1.0% and 0.25%.

We claim:

1. Method of inhibiting a phytophagous insect or arachnid which comprises applying to a locus of the insect or arachnid an effective insect- or arachnid-inactivating amount of an active agent which is a compound of the formula

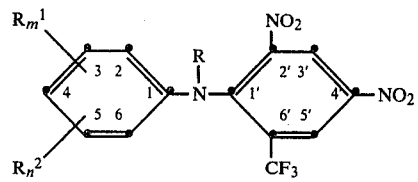

wherein
R=methyl, ethyl, or n-propyl; each $R^1$ is independently bromo, chloro, or fluoro;
$R^2$ is iodo, cyano, nitro, or trifluoromethyl;
m is an integer of from 0 to 5;
n is an integer of from 0 to 1;
and the sum of m and n is an integer
(1) when n is 0, from 1 to 5; and
(2) when n is 1, from 1 to 3
subject to the further limitations that (1) not more than two $R^1$ groups represent bromo; (2) where $R^2$=iodo, the iodo is located at the 4-position; (3) where $R^2$=cyano, the cyano is located at the 3-, 4-, or 5-position; and (4) where $R^2$=$NO_2$, the $NO_2$ is located at the 2-, 3-, 5-, or 6-position.

2. The method of claim 1 which comprises applying the active agent to the locus of an arachnid.

3. The method of claim 2 wherein, in the active agent, R is methyl.

4. The method of claim 3 wherein the active agent is N-methyl-4-fluoro-2',4'-dinitro-6'-(trifluoromethyl)diphenylamine.

5. The method of claim 3 wherein the active agent is N-methyl-2,4-difluoro-2',4'-dinitro-6'-(trifluoromethyl)-diphenylamine.

6. The method of claim 3 wherein the active agent is N-methyl-3,4-difluoro-2',4'-dinitro-6'-(trifluoromethyl)-diphenylamine.

7. The method of claim 3 wherein the active agent is N-methyl-2,4,6-trifluoro-2',4'-dinitro-6'-(trifluoromethyl)diphenylamine.

8. The method of claim 3 wherein the active agent is N-methyl-4-bromo-2',4'-dinitro-6'-(trifluoromethyl)diphenylamine.

9. The method of claim 3 wherein the active agent is N-methyl-4-chloro-2',4'-dinitro-6'-(trifluoromethyl)diphenylamine.

10. The method of claim 3 wherein the active agent is N-methyl-3-(trifluoromethyl)-2',4'-dinitro-6'-(trifluoromethyl)diphenylamine.

11. The method of claim 3 wherein the active agent is N-methyl-2-bromo-4-fluoro-2',4'-dinitro-6'-(trifluoromethyl)diphenylamine.

12. The method of claim 3 wherein the active agent is N-methyl-2-chloro-4-fluoro-2',4'-dinitro-6'-(trifluoromethyl)diphenylamine.

13. The method of claim 3 wherein the active agent is N-methyl-2,4-difluoro-6-chloro-2',4'-dinitro-6'-(trifluoromethyl)diphenylamine.

14. The method of claim 3 wherein the active agent is N-methyl--2,4-difluoro-6-bromo-2',4'-dinitro-6'-(trifluoromethyl)-diphenylamine.

15. Method of inhibiting a phytophagous mite which comprises applying to a plant a miticidally effective amount of an active agent which is a compound of the formula

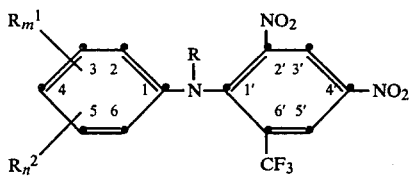

wherein
R=methyl, ethyl, or n-propyl; each $R^1$ is independently bromo, chloro, or fluoro;
$R^2$ is iodo, cyano, nitro, or trifluoromethyl;
m is an integer of from 0 to 5;
n is an integer of from 0 to 1;
and the sum of m and n is an integer
(1) when n is 0, from 1 to 5; and
(1) when n is 1, from 1 to 3
subject to the further limitations that (1) not more than two $R^1$ groups represent bromo; (2) where $R^2$=iodo, the iodo is located at the 4-position; (3) where $R^2$=cyano, the cyano is located at the 3-, 4-, or 5-position; and (4) where $R^2$=$NO_2$, the $NO_2$ is located at the 2-, 3-, 5-, or 6-position.

16. The method of claim 15 wherein, in the active agent, R is methyl.

17. The method of claim 16 wherein the active agent is N-methyl-4-fluoro-2′,4′-dinitro-6′-(trifluoromethyl)-diphenylamine.

18. The method of claim 16 wherein the active agent is N-methyl-2,4-difluoro-2′,4′-dinitro-6′-(trifluoromethyl)diphenylamine.

19. The method of claim 16 wherein the active agent is N-methyl-3,4-difluoro-2′,4′-dinitro-6′-(trifluoromethyl)diphenylamine.

20. The method of claim 16 wherein the active agent is N-methyl-2,4,6-trifluoro-2′,4′-dinitro-6′-(trifluoromethyl)diphenylamine.

21. The method of claim 16 wherein the active agent is N-methyl-4-bromo-2′,4′-dinitro-6′-(trifluoromethyl)-diphenylamine.

22. The method of claim 16 wherein the active agent is N-methyl-4-chloro-2′,4′-dinitro-6′-(trifluoromethyl)-diphenylamine.

23. The method of claim 16 wherein the active agent is N-methyl-3-(trifluoromethyl)-2′,4′-dinitro-6′-(trifluoromethyl)diphenylamine.

24. The method of claim 16 wherein the active agent is N-methyl-2-bromo-4-fluoro-2′,4′-dinitro-6′-(trifluoromethyl)diphenylamine.

25. The method of claim 16 wherein the active agent is N-methyl-2-chloro-4-fluoro-2′,4′-dinitro-6′-(trifluoromethyl)diphenylamine.

26. The method of claim 16 wherein the active agent is N-methyl-2,4-difluoro-6-chloro-2′,4′-dinitro-6′-(trifluoromethyl)diphenylamine.

27. The method of claim 16 wherein the active agent is N-methyl-2,4-difluoro-6-bromo-2′,4′-dinitro-6′-(trifluoromethyl)diphenylamine.

28. Compound of the formula

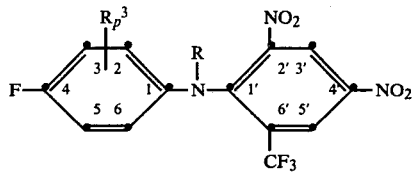

wherein R is methyl, ethyl, or n-propyl; and $R_p^3$ is one of the following:
(1) p=0;
(2) p=1 and $R^3$=2-F, 3-F, 2-Cl, or 2-Br;
(3) p=2, and $R^3$=2-F-6-Br or 2-F-6Cl; or
(4) p=2, 3, or 4 and each $R^3$=F.

29. The compound of claim 28 wherein R=methyl.

30. The compound of claim 29 which is N-methyl-4-fluoro-2′,4′-dinitro-6′-(trifluoromethyl)-diphenylamine.

31. The compound of claim 29 which is N-methyl-2,4-difluoro-2′,4′-dinitro-6′-(trifluoromethyl)-diphenylamine.

32. The compound of claim 29 which is N-methyl-3,4-difluoro-2′,4′-dinitro-6′-(trifluoromethyl)-diphenylamine.

33. The compound of claim 29 which is N-methyl-2,4,6-trifluoro-2′,4′-dinitro-6′-(trifluoromethyl)diphenylamine.

34. The compound of claim 29 which is N-methyl-2-bromo-4-fluoro-2′,4′-dinitro-6′-(trifluoromethyl)diphenylamine.

35. The compound of claim 29 which is N-methyl-2-chloro-4-fluoro-2′,4′-dinitro-6′-(trifluoromethyl)diphenylamine.

36. The compound of claim 29 which is N-methyl-2,4-difluoro-6-chloro-2′,4′-dinitro-6′-(trifluoromethyl)-diphenylamine.

37. The compound of claim 29 which is N-methyl-2,4-difluoro-6-bromo-2′,4′-dinitro-6′(trifluoromethyl)diphenylamine.

38. Composition suitable for controlling insects, arachnides, and ectoparasites, comprising a surface-active dispersing agent and an active agent which is a compound of claim 28.

39. The composition of claim 38 wherein, in the active agent, R=methyl.

40. The composition of claim 39 wherein the active agent is N-methyl-4-fluoro-2′,4′-dinitro-6′-(trifluoromethyl)diphenylamine.

41. The composition of claim 39 wherein the active agent is N-methyl-2,4-difluoro-2′,4′-dinitro-6′-(trifluoromethyl)diphenylamine.

42. The composition of claim 39 wherein the active agent is N-methyl-3,4-difluoro-2′,4′-dinitro-6′-(trifluoromethyl)diphenylamine.

43. The composition of claim 39 wherein the active agent is N-methyl-2,4,6-trifluoro-2′,4′-dinitro-6′-(trifluoromethyl)diphenylamine.

44. The composition of claim 39 wherein the active agent is N-methyl-2-bromo-4-fluoro-2′,4′-dinitro-6′-(trifluoromethyl)diphenylamine.

45. The composition of claim 39 wherein the active agent is N-methyl-2-chloro-4-fluoro-2′,4′-dinitro-6′-(trifluoromethyl)diphenylamine.

46. The composition of claim 39 wherein the active agent is N-methyl-2,4-difluoro-6-chloro-2′,4′-dinitro-6′-(trifluoromethyl)diphenylamine.

47. The composition of claim 39 wherein the active agent is N-methyl-2,4-difluoro-6-bromo-2',4'-dinitro-6'-(trifluoromethyl)diphenylamine.

48. Method of inhibiting insect and acarina parasites on the surface of a warm blooded host animal which comprises applying to the locus of the parasites an effective amount of an active agent which is a compound of the formula

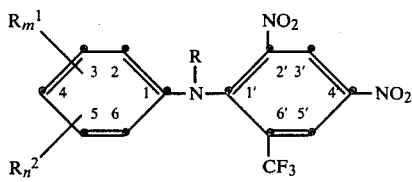

wherein

R = methyl, ethyl, or n-propyl; each $R^1$ is independently bromo, chloro, or fluoro;

$R^2$ is iodo, cyano, nitro, or trifluoromethyl;

m is an integer of from 0 to 5;

n is an integer of from 0 to 1;

and the sum of m and n is an integer
 (1) when n is 0, from 1 to 5; and
 (2) when n is 1, from 1 to 3 subject to the further limitations that (1) not more than two $R^1$ groups represent bromo; (2) where $R^2$=iodo, the iodo is located at only the 4-position ; (3) where $R^2$=cyano, the cyano is located at the 3-, 4-, or 5-position; and (4) where $R^2$=$NO_2$, the $NO_2$ is located at the 2-, 3-, 5-, or 6-position.

49. The method of claim 48 wherein, in the active agent, R is methyl.

50. The method of claim 49 wherein the active agent is N-methyl-2,4-difluoro-2',4'-dinitro-6'-(trifluoromethyl)diphenylamine.

51. The method of claim 49 wherein the active agent is N-methyl-4-bromo-2',4'-dinitro-6'-(trifluoromethyl)diphenylamine.

* * * * *